(12) United States Patent
Ciechanowski

(10) Patent No.: US 8,521,564 B1
(45) Date of Patent: Aug. 27, 2013

(54) COLLABORATIVE HEALTHCARE INFORMATION COLLECTION

(75) Inventor: Paul S Ciechanowski, Seattle, WA (US)

(73) Assignee: Samepage, Inc., Seattle, WA (US)

( * ) Notice: Subject to any disclaimer, the term of this patent is extended or adjusted under 35 U.S.C. 154(b) by 308 days.

(21) Appl. No.: 13/039,608

(22) Filed: Mar. 3, 2011

Related U.S. Application Data

(60) Provisional application No. 61/310,211, filed on Mar. 3, 2010.

(51) Int. Cl.
  *G06Q 50/00* (2012.01)
  *G06Q 10/00* (2012.01)
  *G09G 5/00* (2006.01)
  *G06F 17/00* (2006.01)
  *G06F 17/30* (2006.01)

(52) U.S. Cl.
  USPC ........ 705/3; 705/2; 705/4; 345/594; 345/650; 345/662; 345/676; 707/694; 707/736; 707/758; 707/805

(58) Field of Classification Search
  CPC ................................ G06F 17/00; G06F 17/30
  USPC ....... 705/2–4, 7.14–7.23, 7.27, 14.52–14.58, 705/346; 709/203, 206, 210–215; 717/100–102; 707/600–602, 608–609, 694, 707/705–731, 732, 758, 779, 783–784, 790–792, 707/802–806, 821–828, 736; 345/594, 650, 345/662, 676
  See application file for complete search history.

(56) References Cited

U.S. PATENT DOCUMENTS

| | | | |
|---|---|---|---|
| 6,338,039 B1 * | 1/2002 | Lonski et al. | 705/3 |
| 6,988,075 B1 * | 1/2006 | Hacker | 705/3 |
| 2003/0200117 A1 * | 10/2003 | Manetta et al. | 705/2 |
| 2003/0233257 A1 * | 12/2003 | Matian et al. | 705/3 |
| 2006/0111941 A1 * | 5/2006 | Blom | 705/2 |
| 2006/0259324 A1 * | 11/2006 | Patterson | 705/2 |
| 2006/0277076 A1 * | 12/2006 | Hasan et al. | 705/3 |
| 2007/0174079 A1 * | 7/2007 | Kraus | 705/1 |
| 2007/0273697 A1 * | 11/2007 | Zaman et al. | 345/501 |
| 2008/0040151 A1 * | 2/2008 | Moore | 705/2 |

(Continued)

FOREIGN PATENT DOCUMENTS

WO  WO 2006/122324  * 11/2006

OTHER PUBLICATIONS

Beyette, F.R. et al. "Point-of-Care Technologies for Health Care" IEEE Transactions on Biomedical Engineering, vol. 58, No. 3, Mar. 2011, pp. 732-735.*

(Continued)

*Primary Examiner* — Srirama Channavajjala
(74) *Attorney, Agent, or Firm* — Jensen & Puntigam, P.S.

(57) ABSTRACT

Technologies relating to collaborative healthcare information collection are disclosed. A User Interface (UI) provided herein may provide selectable controls for accessing a Patient Information Collection Tool (PICT), an Interactive Patient Education Database (IPED), and/or a Clinic-Oriented Patient Information Collection Tool (COPICT). A PICT may assist in identifying patient goals for healthcare interactions. An IPED may provide interactive articles educating patients about healthcare terminology and materials for systematically helping patients to prepare for healthcare visits by addressing common questions and discussion points. A COPICT may collect patient data for use in tracking clinic patient data and identifying clinic goals for healthcare interactions.

14 Claims, 19 Drawing Sheets

(56) References Cited

U.S. PATENT DOCUMENTS

| | | | |
|---|---|---|---|
| 2008/0195420 A1* | 8/2008 | Ramelson et al. | 705/3 |
| 2008/0215376 A1* | 9/2008 | Engelman | 705/4 |
| 2009/0055221 A1* | 2/2009 | Loftus et al. | 705/3 |
| 2009/0150292 A1* | 6/2009 | Trinh et al. | 705/55 |
| 2009/0228303 A1* | 9/2009 | Faulkner et al. | 705/3 |
| 2012/0278094 A1* | 11/2012 | Kovacevic et al. | 705/2 |
| 2012/0284056 A1* | 11/2012 | Hofstetter | 705/3 |
| 2012/0284057 A1* | 11/2012 | Hasan et al. | 705/3 |
| 2013/0110542 A1* | 5/2013 | Iyer et al. | 705/3 |

OTHER PUBLICATIONS

Fahad Al-Naydi et al. "A Conceptual Framework for Ubiquitously Sharing Heterogeneous Patient Information among Autonomous Healthcare Providers ", 2007 International Conference on Multimedia andUbiquitous Engineering(MUE'07) Ubiquitous Engineering(MUE'07), pp. 1-6.*

AHRQ, "Build Your Question List", available at http://www.ahrq.gov/questionsaretheanswer/questionBuilder.aspx#Q3 on Jun. 29, 2011.

American Hospital Association, "Eye on Patients: A report from the American Hospital Association and the Picker Institute", 1997.

Committee on Quality Health Care in America, "Crossing the Quality Chasm: A New Health System for the 21st Century", National Academy Press 2001.

Hsiao et al., "Electronic Medical Record/Electronic Health Record Use by Office-based Physicians: United States, 2008 and Preliminary 2009" National Center for Health Statistics, Centers for Disease Control 2009.

Linder et al., "Barriers to electronic health record use during patient visits", AMIA Annual Symposium Proceedings, 2006, pp. 499-503.

Marvel et al., "Soliciting the patient's agenda: have we improved?" JAMA 1999, 281(3): pp. 283-287.

Beckman et al., "The effect of physician behavior on the collection of data", Ann. Intern. Med. 1984, vol. 101, pp. 692-696.

Flocke et al, "Direct observation and patient recall of health behavior advice" Prev. Med. 2004, 38(3): p. 343-349.

The Physicians' Foundation, "The Physicians' Perspective: Medical Practice in 2008", 2008.

Anderson, "Chronic Conditions: Making the case for ongoing care", Johns Hopkins University 2007.

Shappert et al., "Ambulatory Medical Care Utilization Estimates for 2006" National Center for Health Statistics, Centers for Disease Control 2006.

Anderson, "Patient empowerment and the traditional medical model: A case of irreconcilable differences?" Diabetes Care 1995, vol. 18(3), pp. 412-415.

Heszen-Klemens et al., "Doctor-patient interactions, patients' health behavior and effects of treatment", Soc. Sci. and Med. 1984 vol. 19, pp. 19-28.

Squier, "A model of empathic understanding and adherence to treatment regimens in practitioner-patient relationships" Soc. Sci. Med. 1990 vol. 30(3) pp. 325-339.

Wilson, "Promoting compliance: the patient-provider partnership", Adv. Ren. Replace Ther. 1995, vol. 2(3) (Abstract).

Hall et al., "Meta-analysis of correlates of provider behavior in medical encounters", Med. Care 1988, vol. 26(7), pp. 657-675.

Daltroy et al., "Doctor-patient communication and adherence to arthritis treatments", Arthritis Care Res. 1992, 5:S19. (Abstract).

Tessler et al., "Factors affecting the choice between prepaid group practice and alternative insurance programs" Milbank Mem. Fund Q. Health Soc. 1975, vol. 53(2) (Abstract).

Ware et al., "Behavioral consequences of consumer dissatisfaction with medical care", Eval. Program Plann. 1983, vol. 6(3-4), pp. 291-298.

Levinson et al., "Physician-patient communication: The relationship with malpractice claims among primary care physicians and surgeons", JAMA 1997, vol. 277(7), pp. 553-559.

Anderson et al., "Health- care communication and selected psychosocial correlates of adherence in diabetes management." Diabetes Care 1990; vol. 13, pp. 66-76.

Stewart et al., "Interpersonal processes of care in diverse populations", Milbank Q. 1999, vol. 77(3), pp. 305-339.

Roter et al., "Effectiveness of interventions to improve patient compliance: a meta-analysis", Med. Care 1998, vol. 36 (8), pp. 1138-1161.

Kaplan et al., "Assessing the effects of physician-patient interactions on the outcomes of chronic disease", Med. Care 1989, vol. 27(3 Suppl), pp. S110-S127.

Golin et al., "The role of patient participation in the doctor visit. Implications for adherence to diabetes care", Diabetes Care 1996, vol. 19(10), pp. 1153-1164.

Glasgow et al., "Report of the health care delivery work group: behavioral research related to the establishment of a chronic disease model for diabetes care", Diabetes Care 2001, vol. 24(1), pp. 124-130.

Heisler et al., "The relative importance of physician communication, participatory decision making, and patient understanding in diabetes self-management", J. Gen. Intern. Med. 2002, vol. 17(4), pp. 243-252.

Piette et al., "Dimensions of patient-provider communication and diabetes self-care in an ethnically diverse population", J. Gen. Intern. Med. 2003, vol. 18(8), pp. 624-633.

Sherbourne et al., "Antecedents of adherence to medical recommendations: results from the Medical Outcomes Study", J. Behav. Med. 1992, vol. 15(5), pp. 447-468.

Olivarius et al., "Randomised controlled trial of structured personal care of type 2 diabetes mellitus", BMJ 2001, vol. 323(7319), pp. 970-975.

Brown et al., "Promoting patient participation and shortening cancer consultations: a randomised trial", Br. J. Cancer. 2001, vol. 85(9), pp. 1273-1279.

DiMatteo et al., "Physicians' characteristics influence patients' adherence to medical treatment: results from the Medical Outcomes Study", Health Psychol. 1993, vol. 12(2), pp. 93-102.

* cited by examiner

User Interface 300

Instructions:

Status Bar: 0%

Please take a moment to think of the issues you would like to bring up at your next health visit.

Starting with the First Issue box, type in phrases or sentences that describe the health issues you want to cover at your next visit. You do not need to fill in all of the boxes.

| First Issue | Second Issue | Third Issue |
|---|---|---|
| Field 301<br><br>[I've had a sore mouth for two months] | Field 302<br><br>[shortness of breath] | Field 303 |

BACK    NEXT

FIG. 3

User Interface 400

Instructions:

Status Bar: 10%

Enter a one or two word description of each issue.

This is the first issue you listed: Field 301 [I've had a sore mouth for two months]

Please provide a one or two word description of this issue.

Field 401
[sore mouth]

BACK    NEXT

FIG. 4

User Interface 500

Instructions:      Status Bar: 20%

This is the first issue you listed: Field 401: [sore mouth]

Select which aspects of care related to this issue you would like to address at your next visit Click on any icon for more information from the educational database

| Icon 501 | ☑ Diagnosis 502 | Icon 503 | ☑ Refill 504 |
| Icon 505 | ☑ Information 506 | Icon 507 | ☑ Support 508 |
| Icon 509 | ☑ Prognosis 510 | Icon 511 | ☑ Stress 512 |
| Icon 513 | ☑ Tests 514 | Icon 515 | ☑ Function 516 |
| Icon 517 | ☑ Treatment Options 518 | Icon 519 | ☑ Referral 520 |
| Icon 521 | ☑ Medications 522 | Icon 523 | ☑ Paperwork 524 |

Other: ☑    Field 530 [Determine if related to drinking coffee]

BACK    NEXT

FIG. 5

User Interface 700

Instructions:     Status Bar: 50%

Is there another issue you would like to discuss at your next healthcare visit?

If yes, type a description of the issue in the space provided, then click next. If not, just click next.

Field 701

BACK     NEXT

User Interface 800

Instructions:     Status Bar: 60%

Below are issues that you listed. Move the issues into order of importance by dragging them. Put the most important issue at the top and the least important issue at the bottom.

Keep in mind that your provider may only be able to help you with your high-priority issues during your visit. This will depend on how complex your issues are and how much time is slated for the visit.

Priority Position 801
[Priority 1]

Priority Control 811
Field 301: [sore mouth]

Priority Position 802
[Priority 2]

Priority Control 812
Field 302: [shortness of breath]

BACK     NEXT

FIG. 8

User Interface 900

Instructions:

Status Bar 80%

How I like to receive health information.

We all receive and remember information in different ways. Check each of the ways that you like to receive information and will best help you remember what is discussed during your visit.

- ☑ Verbal Instructions 901
- ☑ Written Instructions 902
- ☑ Figures or Graphs 903
- ☑ Information Pamphlets 904
- ☑ Audio-taping of my visits 905
- ☑ Getting an opportunity to ask questions 906
- ☑ Taking Notes 907
- ☑ Getting emailed information 908
- ☑ Web-based information 909
- ☑ Audiovisual materials 910
- ☑ Interacting in Groups 911
- ☑ Bringing someone to the visit with me 912

Other: ☑  Field 920

BACK  NEXT

FIG. 9

Report 1100

Field 1111: Patient ID | Field 1112: Date 2

Instructions: Please bring two copies of this form to your next healthcare visit – one for your and one for your healthcare provider.

This form was completed on: Field 1121: Date 1

The main issues I want to bring up at this healthcare visit:

1. Field 1131
   Field 301 (or 401): [sore mouth]
   Seeking help with:
   Field 1132: Selected Aspects of Care
   Notes:

2. Field 1141
   Field 302: [shortness of breath]
   Seeking help with:
   Field 1142: Selected Aspects of Care
   Notes:

Issues to bring if there is enough time or at my next healthcare visit:

3. Field 1151
   Field 303
   Seeking help with:
   Field 1152: Selected Aspects of Care 4. Field 1161
   Field 3XX
   Seeking help with:
   Field 1162: Selected Aspects of Care 5. Field 1171
   Field 3XY
   Seeking help with:
   Field 1172: Selected Aspects of Care Notes:

Ways I would like to receive information

Field 1182: Selected Information Channels

FIG. 11

User Interface 1400

Instructions:
The following are things you can ask or tell your provider to get the most from your healthcare visits related to getting tests:

Ask:
- ☑ What is the test?
- ☑ Where do I get the test or procedure done?
- ☑ Who is doing it?
- ☑ Why am I getting this test?
- ☑ When do I get it?
- ☑ How and when will I get the results?
- ☑ How will I know what the results mean?
- ☑ Who will tell me what the results mean?
- ☑ Are there any downsides or risks to getting this test?
- ☑ Do I have to restrict what I eat or drink before the test?
- ☑ How do I prepare for the test?
- ☑ Is this test partially or fully covered by insurance? (you may have to speak directly with a representative from your insurance plan)
- ☑ Other: | Field 1401 |

Tell:
- ☑ If you have had a similar test done before and what the result was.
- ☑ Your fears and concerns about the test or test results
- ☑ Who in your family you would like to share the results with
- ☑ How you would like to receive the results
- ☑ Other: | Field 1402 |

View / Print Selections 1403

FIG. 14

User Interface 1500

Instructions:

The following are things you chose to ask or tell your provider at your next healthcare visit:

- ☑ What is the test?
- ☑ Who will tell me what the results mean?
- ☑ Are there any downsides or risks to getting this test?
- ☑ How do I prepare for the test?
- ☑ How you would like to receive the results

User Interface 1700

Patient Query 1701 — Status Bar: 10%

In the PAST 12 MONTHS have you had a test for glaucoma performed by an eye doctor (e.g. ophthalmologist or optometrist)?

☑ Yes  ☑ No  ☑ Not Sure — Response Field(s) 1702

Information Section 1703

What is glaucoma?

Glaucoma is a group of diseases where the fluid pressure of the eye rises slowly. Glaucoma can cause vision loss or blindness by damaging one of the eye's main nerves, called the optic nerve.

A test for glaucoma is called tonometry and looks like this:

Image 1704

BACK   NEXT

Report 2100

Field 2111: Patient ID     Field 2112: Date 2

Instructions: Please bring 1 copy of this form to your next healthcare visit.

This form was completed on: Field 2121: Date 1

Section 2130

In the past 6 months, I received the following from a doctor:

| Field 2132 [Yes/No/Not Sure/ Not Applicable] | Content Element 2131 Treatment for urinary incontinence (UI). |

Section 2140

In the past 12 months, I received the following from a doctor:

| Field 2144 [Yes/No/Not Sure/ Not Applicable] | Content Element 2141 An eye test for glaucoma prepared by an eye doctor. |

| Field 2145 [Yes/No/Not Sure/ Not Applicable] | Content Element 2142 Advice about starting, maintaining, or increasing physical exercise. |

| Field 2146 [Yes/No/Not Sure/ Not Applicable] | Content Element 2143 A 6-month or longer prescription of medications (that may need monitoring) from among the following classes: ACE inhibitors, ARBs, digoxin, diuretics, anticonvulsants, statins. |

Field 2147: [lisinopril; digoxin; hydrochlorothiazide; lovastatin]

Section 2150

In the past 24 months:

| Field 2152 [Yes/No/Not Sure/ Not Applicable] | Content Element 2151 I received a mammogram test for breast cancer screening. |

FIG. 21

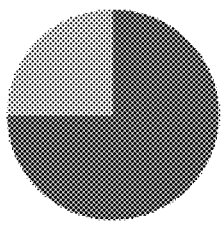
CHART 1
Initial Diagnosis - Patient Questions
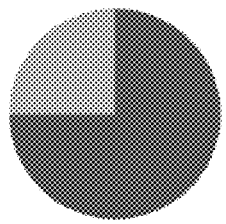
CHART 2
Initial Diagnosis – Doctor Answers
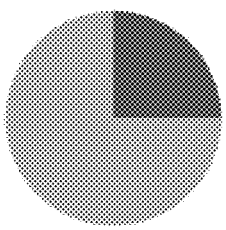
CHART 3
Established Diagnosis - Patient Questions
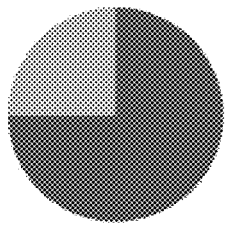
CHART 4
Established Diagnosis – Doctor Answers
FIG. 22

COLLABORATIVE HEALTHCARE INFORMATION COLLECTION

CROSS REFERENCE TO RELATED APPLICATIONS

Priority is claimed to U.S. Provisional Application No. 61/310,211, filed Mar. 3, 2010, entitled "PATIENT INFORMATION COLLECTION TOOL", which is incorporated by reference herein.

BACKGROUND

The prevailing U.S. healthcare system has a number of characteristics that negatively impact healthcare communication and limit opportunities for relationship and trust building among patients and clinicians. See, e.g., *American Hospital Association, "Eye on Patients: A report from the American Hospital Association and the Picker Institute"*, 1997; *Committee on Quality Health Care in America, "Crossing the Quality Chasm: A New Health System for the 21st Century", National Academy Press* 2001. As a result of significant time constraints and competing demands, healthcare providers are often perceived as being rushed and impersonal by their patients. Information exchange among patients' healthcare providers can be fragmented because of lack of integrated information systems, e.g. according to a 2009 Center for Disease Control (CDC) national mail survey, a minority of physicians (43.9%) reported using full or partial electronic medical record/electronic health record systems (not including systems solely for billing) in their office-based practices. Only 20.5% reported having systems that met the criteria of a basic system, and only 6.3% reported having a fully functional system, a subset of a basic system. Hsiao et al., *"Electronic Medical Record/Electronic Health Record Use by Office-based Physicians: United States,* 2008 *and Preliminary* 2009*" National Center for Health Statistics, Centers for Disease Control* 2009.

While technological advances undoubtedly improve medical care, such advances can undermine the quality of patient-provider communication. Increasing clinician emphasis on imaging, laboratory tests, and procedures can move the patient-provider dialogue away from patients' day-to-day issues in managing illness and toward an emphasis on solutions that are biomedical and procedure-based. Furthermore, with increased inclusion of computers in busy medical offices, patients complain that clinicians' eyes are increasingly averted away from them and toward computer screens. Linder et al., *"Barriers to electronic health record use during patient visits", AMIA Annual Symposium Proceedings,* 2006, pages 499-503.

Even under ideal conditions, healthcare providers and patients may fundamentally see medical issues from different perspectives, for example as outlined in the table below.

TABLE 1

Differences in communication foci between patients and healthcare providers (e.g. doctors): Patients' day-to-day experiences with symptoms and management of chronic conditions often contrasts with the biomedical view of a doctor.

| PATIENT (LIVES) | DOCTOR (WORKS) |
| --- | --- |
| EXPERIENTIAL | DIAGNOSTIC |
| DAY-TO-DAY | SNAPSHOT VIEW |
| PATIENT'S EXPLANATORY MODEL | DOCTOR'S MEDICAL MODEL |

TABLE 1-continued

Differences in communication foci between patients and healthcare providers (e.g. doctors): Patients' day-to-day experiences with symptoms and management of chronic conditions often contrasts with the biomedical view of a doctor.

| PATIENT (LIVES) | DOCTOR (WORKS) |
| --- | --- |
| SYMPTOMS | SIGNS/TEST RESULTS |
| FUNCTION/QUALITY OF LIFE | MEDICAL OUTCOME |

Even greater divergence may potentially take place once a diagnosis is established and treatment is under way. At initial diagnosis, patients predominantly have questions about the type of condition ("what") and cause ("why") which biomedically trained healthcare providers are able to respond to, for example as illustrated in CHART 1 and CHART 2 in FIG. 22.

After an established diagnosis, however, patients' focus is more often on day-to-day management ("how", "where", "when", "who") than on the pathophysiological explanations of the condition. Healthcare providers are often less effective at answering these questions, as illustrated CHART 3 and CHART 4 in FIG. 22.

The lack of collaboration between patients and physicians has also been demonstrated in research involving analysis of audio taped healthcare visits that shows that physicians' patterns of practice can significantly limit mutual exchange. In two separate studies it was shown that at the start of a health visit, physicians interrupt patients and begin to control the content and direction of the appointment within 18 to 23 seconds, on average. Marvel et al., *"Soliciting the patient's agenda: have we improved?" JAMA* 1999, 281(3): pages 283-287; Beckman et al., *"The effect of physician behavior on the collection of data", Ann. Intern. Med.* 1984, vol. 101, pages 692-696. Lack of collaboration and inattention to communication quality or consideration of how patients best learn and retain information contribute to poor patient recall of medical recommendations. In a study of 2600 patient-provider dyads where health visits were observed and patients were interviewed immediately after the visit, it was shown that patients recall only 50% of medical recommendations at the time of exit interviews. Flocke et al., *"Direct observation and patient recall of health behavior advice" Prev. Med.* 2004, 38(3): pages 343-349.

Health professionals find it increasingly hard to communicate in the way that they and their patients would like. In a recent survey of doctors in the US, 'patient relationships' ranked highest on the list of things doctors find most satisfying about medicine, yet only one third of surveyed doctors reported having enough time to fully communicate with and treat their patients. *The Physicians' Foundation, "The Physicians' Perspective: Medical Practice in* 2008", 2008. Meaningful face-to-face time between patient and doctor has been whittled away by paperwork and administrative tasks, and the complexity of treating co-existing conditions requires that more time is spent gathering data and test results, leaving less time to hear peoples' stories and develop meaningful relationships.

These healthcare system limitations and practice patterns exist at a time when—with an aging population—there are proportionately greater numbers of patients with chronic conditions than ever before. Currently, 130 million individuals in the U.S. have at least one chronic condition and 75 million Americans have 2 or more chronic conditions. Anderson, *"Chronic Conditions: Making the case for ongoing care", Johns Hopkins University* 2007. Compared to treatment of acute conditions, chronic conditions require greater emphasis on patient-provider collaboration, more education of patients about their conditions, increased preparation for visits, and greater active participation by patients and their family members. Healthcare visit length has not increased in proportion with the time required for patients and providers to managing multiple chronic conditions. In fact, the Centers for Disease Control estimates that the average length of a primary care visit in the U.S. is approximately 20 minutes, of which a only portion is effective face-to-face time. Schapert et al., "*Ambulatory Medical Care Utilization Estimates for 2006*" *National Center for Health Statistics, Centers for Disease Control* 2006.

Taking steps to improve the level of communication between patient and provider is a worthwhile effort. In addition to leading to improved patient satisfaction, there is abundant research showing that increased quality of patient-provider communication is associated with better outcomes. For example, across illnesses, treatment adherence and outcomes improve when patients are empowered, experience enhanced emotional patient-provider exchanges, sense they are equal partners with providers, perceive providers as empathic, negotiate around treatments, and actively communicate with providers. See Anderson, "*Patient empowerment and the traditional medical model: A case of irreconcilable differences?*" *Diabetes Care* 1995, vol. 18(3), pages 412-415; DiMatteo et al., "*Physicians' characteristics influence patients' adherence to medical treatment: results from the Medical Outcomes Study*", *Health Psychol.* 1993, vol. 12(2), pages 93-102; Haszen-Kelmens et al., "*Doctor-patient interactions, patients' health behavior and effects of treatment*", *Soc. Sci. and Med.* 1984 vol. 19, pages 19-28; Squier, "*A model of empathic understanding and adherence to treatment regimens in practitioner-patient relationships*" *Soc. Sci. Med.* 1990 vol. 30(3) pages 325-339; Wilson, "*Promoting compliance: the patient-provider partnership*", *Adv. Ren. Replace Ther.* 1995, vol. 2(3), pages 199-206; Hall et al., "*Meta-analysis of correlates of provider behavior in medical encounters*", *Med. Care* 1988, vol. 26(7), pages 657-675; Daltroy et al., "*Doctor-patient communication and adherence to arthritis treatments*", *Arthritis Care Res.* 1992, 5:S19.

Conversely, poor patient-provider communication is associated with lower treatment adherence, lower satisfaction with care, greater health plan disenrollment, greater provider switching, and greater malpractice risk. See Tessler et al., "*Factors affecting the choice between prepaid group practice and alternative insurance programs*" *Milbank Mem. Fund Q. Health Soc.* 1975, vol. 53(2), pages 149-172; Ware et al., "*Behavioral consequences of consumer dissatisfaction with medical care*", *Eval. Program Plann.* 1983, vol. 6(3-4), pages 291-298; Levinson et al., "*Physician-patient communication: The relationship with malpractice claims among primary care physicians and surgeons*", *JAMA* 1997, vol. 277(7), pages 553-559.

Higher quality patient-provider interactions are associated with better disease self-management efforts, better treatment adherence, and improved control of glucose, lipids and blood pressure, as demonstrated through controlled trial evidence. See Anderson et al. "*Health-care communication and selected psychosocial correlates of adherence in diabetes management.*" *Diabetes Care* 1990; vol. 13, pages 66-76; Stewart et al. "*Interpersonal processes of care in diverse populations*", *Milbank Q.* 1999, vol. 77(3), pages 305-339; Roter et al. "*Effectiveness of interventions to improve patient compliance: a meta-analysis*", *Med. Care* 1998, vol. 36(8), pages 1138-1161; Kaplan et al. "*Assessing the effects of physician-patient interactions on the outcomes of chronic disease*", *Med. Care* 1989, vol. 27(3 Suppl), pages 5110-127 (hereinafter Kaplan); Golin et al. "*The role of patient participation in the doctor visit. Implications for adherence to diabetes care*", *Diabetes Care* 1996, vol. 19(10), pages 1153-1164; Glasgow et al. "*Report of the health care delivery work group: behavioral research related to the establishment of a chronic disease model for diabetes care*", *Diabetes Care* 2001, vol. 24(1), pages 124-130; Heisler et al. "*The relative importance of physician communication, participatory decision making, and patient understanding in diabetes self-management*", *J. Gen. Intern. Med.* 2002, vol. 17(4), pages 243-252; Piette et al. "*Dimensions of patient-provider communication and diabetes self-care in an ethnically diverse population*", *J. Gen. Intern. Med.* 2003, vol. 18(8), pages 624-633; Sherbourne et al. "*Antecedents of adherence to medical recommendations: results from the Medical Outcomes Study*", *J. Behav. Med.* 1992, vol. 15(5), pages 447-468; Olivarius et al. "*Randomised controlled trial of structured personal care of type* 2 *diabetes mellitus*", *BMJ* 2001, vol. 323(7319), pages 970-975.

Specific use of point-of-service prompt sheets (i.e. where a patient's questions are prepared and conveyed during the healthcare visit and where healthcare provider and patient both engage in using the prompt sheet) has been shown to be associated with increased recall, decreased patient anxiety, potential decrease in length of visit and improved metabolic control. See Kaplan, cited above; Brown et al., "*Promoting patient participation and shortening cancer consultations: a randomised trial*", *Br. J. Cancer.* 2001, vol. 85(9), pages 1273-1279.

SUMMARY

Technologies relating to collaborative healthcare information collection are disclosed. A User Interface (UI) provided herein may provide selectable controls for accessing a Patient Information Collection Tool (PICT), an Interactive Patient Education Database (IPED), and/or a Clinic-Oriented Patient Information Collection Tool (COPICT). A PICT may assist in identifying patient goals for healthcare interactions. An IPED may provide interactive articles educating patients about healthcare terminology and materials for systematically helping patients to prepare for healthcare visits by addressing common questions and discussion points. A COPICT may collect patient data for use in tracking clinic patient data and identifying clinic goals for healthcare interactions.

BRIEF DESCRIPTION OF THE DRAWINGS

FIG. 3 illustrates a UI provided by example PICT module(s) configured to identify patient health issues.

FIG. 4 illustrates a UI provided by example PICT module(s) configured to assign a short description to one or more identified patient health issues.

FIG. 5 illustrates a UI provided by example PICT module(s) configured to identify a patient's desired aspects of care for one or more identified patient health issues, as well as access an IPED configured to educate the patient about available aspects of care.

FIG. 7 illustrates a UI provided by example PICT module(s) configured to provide a redundant opportunity to identify patient health issues.

FIG. 8 illustrates a UI provided by example PICT module(s) configured to prioritize patient health issues.

FIG. 9 illustrates a UI provided by example PICT module(s) configured to identify desired information channels.

FIG. 11 illustrates an example report as may be generated by PICT modules.

FIG. 14 illustrates a UI that may be provided in connection with a feature of an IPED.

FIG. 15 illustrates a UI that may be provided as an output accessible from a UI such as FIG. 14.

FIG. 17 illustrates an example UI as may be included in a COPICT.

FIG. 21 illustrates an example report as may be generated by COPICT modules.

FIG. 22 provides charts illustrating patient question focus and healthcare provider answer focus, for initial diagnosis and after established diagnosis.

DETAILED DESCRIPTION

Figure 1:
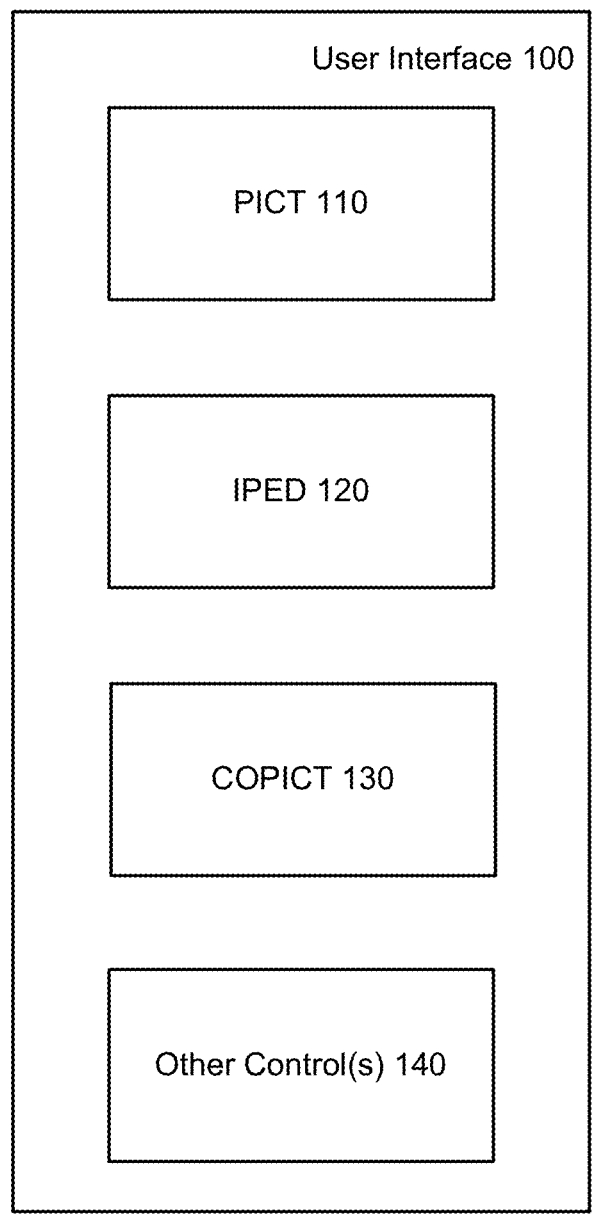
FIG. 1 illustrates a UI comprising selectable controls for accessing a PICT, an IPED, a COPICT, and other controls as may be combined therewith.

The illustrative embodiments provided herein are not meant to be limiting. Other embodiments may be utilized, and changes may be made, without departing from the spirit or scope of the subject matter presented here. It will be understood that aspects of the present disclosure may be arranged, substituted, combined, and designed in a wide variety of different configurations.

Clinical performance may be enhanced by improving the communication quality between patients and their healthcare team. This may be accomplished using the patient-centered engagement tools and related technologies described herein. These technologies improve quality of care, improve patient engagement, help patients prepare for healthcare visits, serve as market differentiators for healthcare providers and organizations, and improve patient and healthcare provider satisfaction. Currently, Medicare Advantage (MA) plans are rated annually and assigned star ratings by the Centers for Medicare and Medicaid Services (CMS) based on clinical and customer service performance. Ratings are posted on the Medicare website to provide beneficiaries information about available programs in their area. Healthcare legislation proposes using these quality ratings to identify and reward high-quality plans. As this and other such rating systems become increasingly important, there will be increased competition in the healthcare industry and an increased need to remain competitive in quality of care as well as customer satisfaction.

Preparing for health visits is associated with significant improvement in patient-provider communication by increasing patient participation and patient satisfaction, increasing question asking for clarification and better understanding, increasing visit recall, decreasing patient anxiety during health visits, and decreasing consultation time. Improved patient-provider communication is associated with greater satisfaction with care, lower rates of health plan disenrollment, lower rates of provider switching, lower malpractice risk, greater information exchange, improved treatment adherence, and improved medical outcomes (e.g. glucose, lipids, blood pressure).

The tools provided herein include a PICT, which may be configured to match patients' issues with healthcare provider services, or aspects of care, during a healthcare visit. In some embodiments, the PICT may also guide expectations around how much can reasonably be covered in a typical follow-up visit, and may address patients' preferred way of receiving information. The PICT may help patients prepare for healthcare visits by allowing them to consider the issues they want to cover, rank those issues in order of importance, determine the specific clinical services they want to focus on, prepare questions or things they want to tell their provider about their issues, and convey how they would like to receive information to improve information retention and recall.

An IPED tool is also provided herein. The IPED provides a platform for systematically helping patients to prepare for healthcare visits by addressing common questions and discussion points. There are countless questions that patients may have before or during a healthcare visit. There are also a number of common questions that patients should consider asking their healthcare providers in order to get the most from their healthcare visits. Similarly, there are a number of common things that healthcare providers will want to know in the process of making a diagnosis or determining a suitable treatment. In some embodiments, the IPED provides a collection of common questions for patients to ask or information items to tell their healthcare providers during the course of a healthcare visit in the areas of one or more of: diagnosis, information, prognosis, tests, treatment options, medications, medication refills, support, stress, function, referral and paperwork.

A COPICT and COPICT builder are also described herein. In some embodiments, a COPICT may be configured to ascertain issues pertaining to guideline and evidence-based indicators. A COPICT may provide a platform that allows a healthcare organization to administer customized questions through a patient-facing UI, allowing the organization to address key quality and guideline-level needs resulting in improved clinical performance. A COPICT may raise awareness of guideline and evidence-based care and related outcomes among patients and healthcare providers to guide organizational change, may identify systemic barriers to completion of preventive care tasks, and may raise awareness not only of multiple ways to record events and tasks, but also of ways to get events/tasks accomplished in the organization's system.

FIG. 1 illustrates a UI comprising selectable controls for accessing a PICT, an IPED, a COPICT, and other controls as may be combined therewith. In some embodiments, the UI 100 may be configured to be rendered on a display such as a computer monitor or a handheld device display screen. For example, the UI 100 may be provided as a webpage available via the internet or other computer network, with the various controls 110, 120, 130, and 140 incorporating links to the indicated tools and/or data. User selections of any of the controls may be made by moving a mouse pointer over a control, then indicating selection thereof by "clicking" on the control with a mouse button. In the case of touch screen displays, user selections may be made for example by touching a display at the location of a desired control.

The UI 100 may comprise a selectable PICT control 110 configured to access a PICT as described herein, for example, a PICT configured to receive one or more patient issues and corresponding selected aspects of care in preparation for a healthcare visit, and to generate a report comprising prioritized identifications of patient issues along with selected aspects of care corresponding to each patient issue.

The UI 100 may comprise a selectable IPED control 120 configured to access an IPED as described herein, for example, an IPED comprising educational information regarding selectable aspects of care accessible via the PICT.

The UI 100 may comprise a selectable COPICT control 130 configured to access a COPICT as described herein, for example, a COPICT configured to receive patient health data corresponding to one or more clinic selected quality indicators.

The UI 100 may comprise other controls 140 configured to access any number of other controls that may be combined with the PICT control 110, IPED control 120, and COPICT control 130. For example, in some embodiments the other controls 140 may be configured to access a language selection tool, allowing selection of a language for the UI 100 as well as tools and data accessible via the UI 100. It will be appreciated that there are a wide variety of additional features and functions that may be beneficially combined with the illustrated controls.

Figure 2:
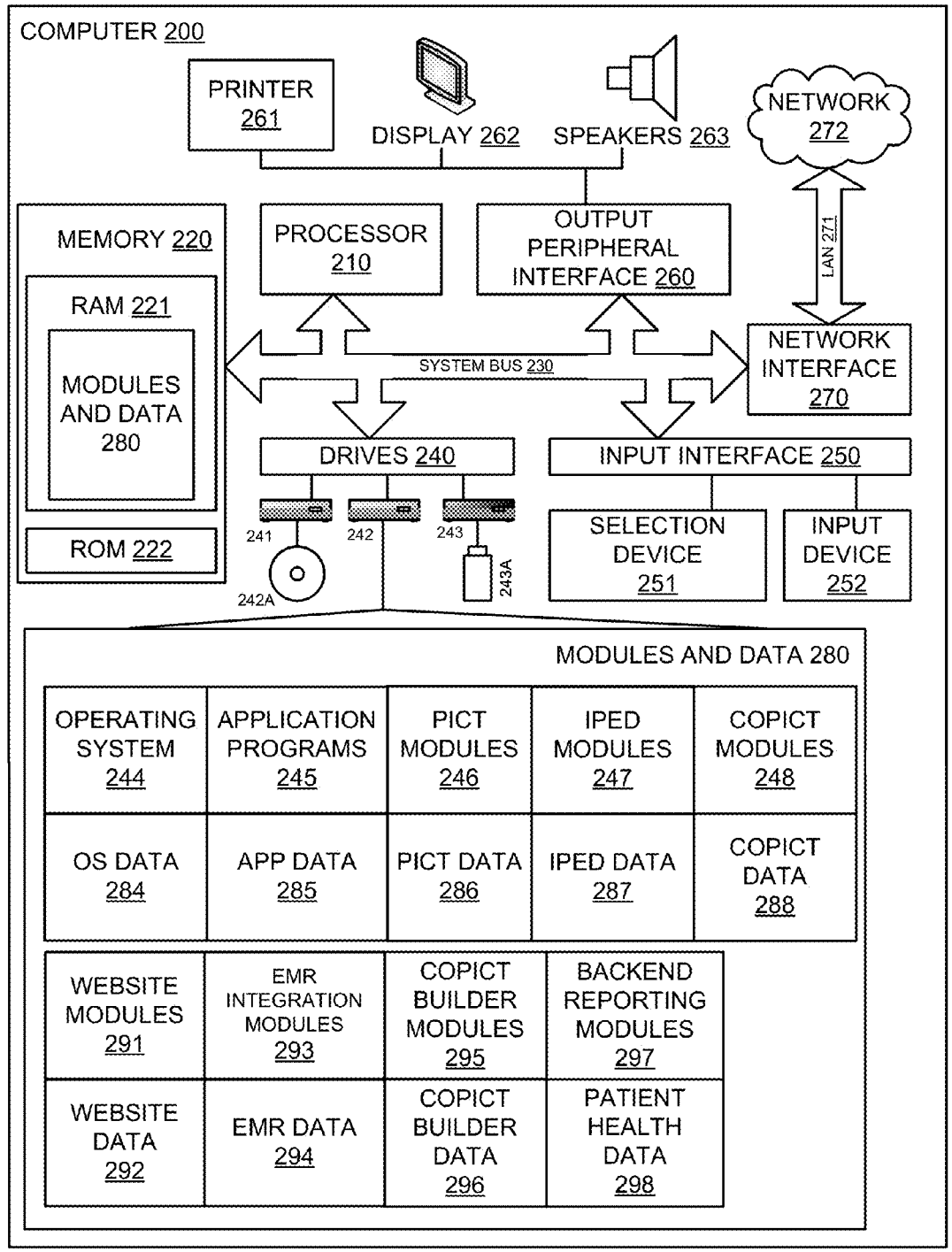
FIG. 2 illustrates a computer configured to implement the technologies disclosed herein.

FIG. 2 is a diagram illustrating an example computer 200 configured to implement various collaborative healthcare information collection technologies disclosed herein. Computer 200 may include for example a processor 210, memory 220, system bus 230, one or more drives 240, user input interface 250, output peripheral interface 260, and network interface 270.

Drives 240 may include, for example, a compact disk drive 241 which accepts an optical disk 241A, a so-called hard drive 242, which may employ any of a diverse range of computer readable media, and a flash drive 243 which may employ for example a Universal Serial Bus (USB) type interface to access a flash memory 243A. Drives may further include network drives and virtual drives (not shown) accessed via the network interface 270.

The drives 240 and their associated computer storage media provide storage of computer readable instructions, data structures, program modules and other data for the computer 200, referred to as modules and data 280. Modules and data 280 may include for example one or more of an operating system 244 and OS data 284, application programs 245 and app data 285, PICT modules 246 and PICT data 286, IPED modules 247 and IPED data 287, COPICT modules 248 and COPICT data 288, website modules 291 and website data 292, Electronic Medical Records (EMR) integration modules 293 and EMR data 294, COPICT builder modules 295 and COPICT builder data 296, backend reporting modules 297 and patient health data 298. Modules and data 280 may be loaded into RAM 221 to implement the UI and carry out the various operations discussed herein.

Computer 200 may further include a wired or wireless input interface 250 through which selection devices 251 and input devices 252 may interact with the other elements of the computer 200. Selection devices 251 and input devices 252 can be connected to the input interface 250 which is in turn coupled to the system bus 230, allowing devices 251 and 252 to interact with processor 210 and the other elements of the computer 200. Interface and bus structures that may be utilized to implement 250 may include for example a Peripheral Component Interconnect (PCI) type interface, parallel port, game port and a wired or wireless Universal Serial Bus (USB) interface.

Selection devices 251 such as a mouse, trackball, touch screen, or touch pad allow a user to select among desired options that may be output by the computer 200, for example via the display 262. Input devices 252 can include any devices through which commands and data may be introduced to the computer 200. Exemplary input devices 252 include a keyboard, an electronic digitizer, a microphone, a joystick, game pad, satellite dish, scanner, media player, mobile device, or the like.

Computer 200 may also include an output peripheral interface 260 which allows the processor 210 and other devices coupled to bus 230 to interact with peripheral output devices such as printer 261, display 262, and speakers 263. Interface and bus structures that may be utilized to implement 260 include those structures that can be used to implement the input interface 250. It should also be understood that many devices are capable of supplying input as well as receiving output, and input interface 250 and output interface 260 may be dual purpose or support two-way communication between components connected to the bus 230 as necessary.

Computer 200 may operate in a networked environment using logical connections to one or more computers. In some embodiments, computer 200 may take the form of a smart phone or other small form-factor device, which may for example connect to a network via a cellular communications connection. By way of example, FIG. 2 shows a LAN 271 connection to a network 272. A remote computer may also be connected to network 272. The remote computer may be a personal computer, a server, a router, a network PC, a peer device or other common network node, and can include many or all of the elements described above relative to computer 200.

When used in a LAN or WLAN networking environment, computer 200 may be connected to the LAN through a network interface 270 or an adapter. When used in a WAN networking environment, computer 200 typically includes a modem or other means for establishing communications over the WAN, such as the Internet or network 272. It will be appreciated that other means of establishing a communications link between computers may be used.

In some example configurations, computer 200 may comprise a web server configured to host a website accessible by client computers, the website configured for client access to one or more of a PICT, an IPED, and/or COPICT. The web server may optionally integrate with an EMR system, e.g., by configuring the web server to populate a PICT and/or COPICT with patient health data stored in an EMR system, and/or by configuring the web server to store patient health data 298 received via the PICT, IPED, or COPICT in an EMR system. In addition to reports generated by the PICT, IPED, and/or COPICT, the web server may be configured to generate any number of backend reports using gathered patient health data 298.

In some example configurations, computer 200 may comprise an administrator terminal configured to provide an administrator interface configured to access PICT modules 246, IPED modules 247, and/or COPICT modules 248. The administrator interface may be configured to receive an identification of a clinic patient, and provide a PICT, IPED, and/or COPICT corresponding to the identified clinic patient. For example, a health coach (or other healthcare professional) may have a caseload comprising multiple patients. An administrator interface may be configured to compile a list of clinic patients corresponding to a health coach caseload, when the health coach logs in to the administrator interface. Upon receiving a patient selection, the administrator interface may be configured to load a PICT, IPED, or COPICT corresponding to the received patient selection. The health coach may then interact with the patient, e.g., in person or by phone, and may enter patient health data 298 into the PICT, IPED, or COPICT based on information gathered from the patient. The administrator terminal may also be configured to integrate with an EMR system, e.g., by configuring the administrator terminal to populate a PICT, IPED and/or COPICT with patient health data stored in an EMR system, and/or by configuring the administrator terminal to store patient health data 298 received via the PICT, IPED, or COPICT in an EMR system.

In some embodiments, health coaches or other healthcare professionals, such as assist navigators and case managers can use the tools provided herein (the PICT, IPED, and/or COPICT) to help patients in their caseload prepare for healthcare visits. There are several ways that such health professionals can use the tools, including for example, in-person, by telephone, and/or through an integrated online service. When in-person, the coach can complete a tool for a patient and provide the patient copies of the completed reports to take to a health appointment. The coach may also distribute completed reports to appropriate recipients on behalf of the patient. When interacting by telephone, the coach may use a tool to inform an interview about preparation for an upcoming health visit. The patient may or may not log into a tool completion session in parallel with the coach. At the end of the coaching call, the coach can provide completed reports to the patient or to the patient's healthcare practitioner, e.g., by emailing or mailing completed reports. When the patient and coach share a web platform (e.g. with integrated login service), the completed reports can be available to the patient when logged in to their account. When interacting by integrated online service, a coach can assist a patient by telephone, web-based platform, web chat, instant messaging, texting, or other communication channel, to complete a tool. In this embodiment, the patient may complete the tool, while a coach directs the patient through the process. The use of health coaches, assist navigators and case managers is consistent with care of chronic conditions and can be an integral part of the "medical home", also known as a patient-centered medical home (PCMH), defined as "an approach to providing comprehensive primary care . . . that facilitates partnerships between individual patients, and their personal providers, and when appropriate, the patient's family". The provision of medical homes may allow better access to healthcare, increase satisfaction with care, and improve health.

In some example configurations, computer 200 may comprise a COPICT builder, comprising COPICT builder modules 295 and COPICT builder data 296 configured to build an individualized COPICT on behalf of an organization, clinic or healthcare provider. A COPICT builder may comprise a library of patient queries, wherein each patient query is designed to retrieve patient health data 298. Patient queries may comprise, for example, questions selected for gathering desired patient health data 298, and may include pictures and explanatory information selected to educate the patient in responding to corresponding questions. A COPICT builder may be configured to receive clinic selected quality indicators, and to build a COPICT comprising patient queries from the library of patient queries corresponding to the clinic selected quality indicators, and fields configured to receive patient health data 298 in response to the patient queries. Once the COPICT is built, the COPICT builder may optionally be configured to export the COPICT for use at another computer, such as a web server, administrator terminal, and/or client computer described herein.

In some example configurations, computer 200 may comprise a client computer, such as a personal computer in laptop or desktop configuration, or a handheld device such as a smart phone. The client computer may access a website via a browser application, or may otherwise run software that provides a PICT, IPED, and/or COPICT. A patient may for example access a website or launch an application that accesses the PICT, IPED, and/or COPICT. The PICT, IPED and/or COPICT may receive patient health data 298 and may generate a report at the client computer. The client computer may be configured to allow the patient to share the report(s) electronically with a healthcare provider, and/or may be configured to allow the patient to print report(s) so that physical copies may be brought to an appointment. It will be appreciated that the PICT, COPICT, and/or IPED may be presented via a variety of presentation platforms, including on paper, with or without carbon copy format, and online via a UI configured to help patients go through the tools, and optionally allowing patients to print paper reports, save reports, email reports, and/or send reports as a file integrated into a web-based platform. Also the patient health data 298 that populates a report may be directed to populate any form of electronic health record or other online portal that patients, clinicians or administrators can use. Current and prior patient health data 298 can be stored and used to compile any number of reports discussed herein.

Additional presentation platforms include smart phones. As will be appreciated, any online UI can be accessed by smart phone, either as a direct view of a website or as a view/functionality modified for use with smart phones. Furthermore, tablets such as iPad(R) type devices may be used by patients as a way of completing an online UI, or by providers during clinical work, as a way of reading/modifying reports. Tablets configured to implement the disclosed tools may be provided to patients in waiting rooms or once the patient is seated in an exam room. Kiosks, e.g., waiting room kiosks, may be configured to allow patients to complete the disclosed tools on a clinic or other health organization's premises. Also, embodiments may make use of various approaches for receiving patient health data 298. In addition to receiving patient health data 298 through UI illustrated herein, Short Mail Service (SMS) or so-called text messaging data may be leveraged in some embodiments, to derive patient health data 298 from patients' phones. Any data transfer or collection technology can be used including current technologies such as voice recognition and instant messaging (e.g. GOOGLE CHAT(R)), or other technologies as may come into use in the future.

It will be appreciated that a wide variety of configurations of computer 200 are possible, from those implemented on a personal computer or laptop, to those implemented on one or more servers, to those implemented on handheld and/or other portable devices, and the invention is not limited to the example configurations described herein.

A PICT, IPED, COPICT and COPICT builder are described in further detail below. FIG. 3-FIG. 12 are directed to various aspects of a PICT, FIG. 13-FIG. 15 are directed to an IPED, and FIG. 16-FIG. 21 are directed to a COPICT and COPICT builder.

Figure 12:
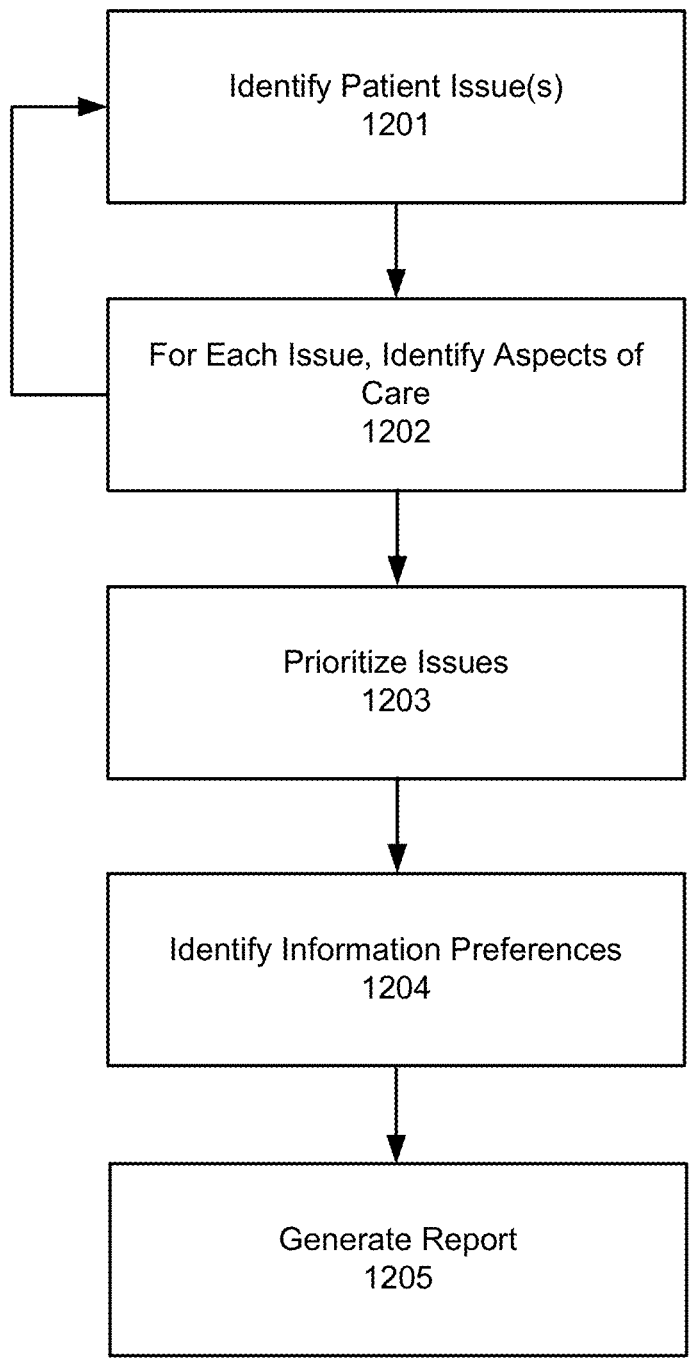
FIG. 12 illustrates an example patient information collection method.
Figure 13:
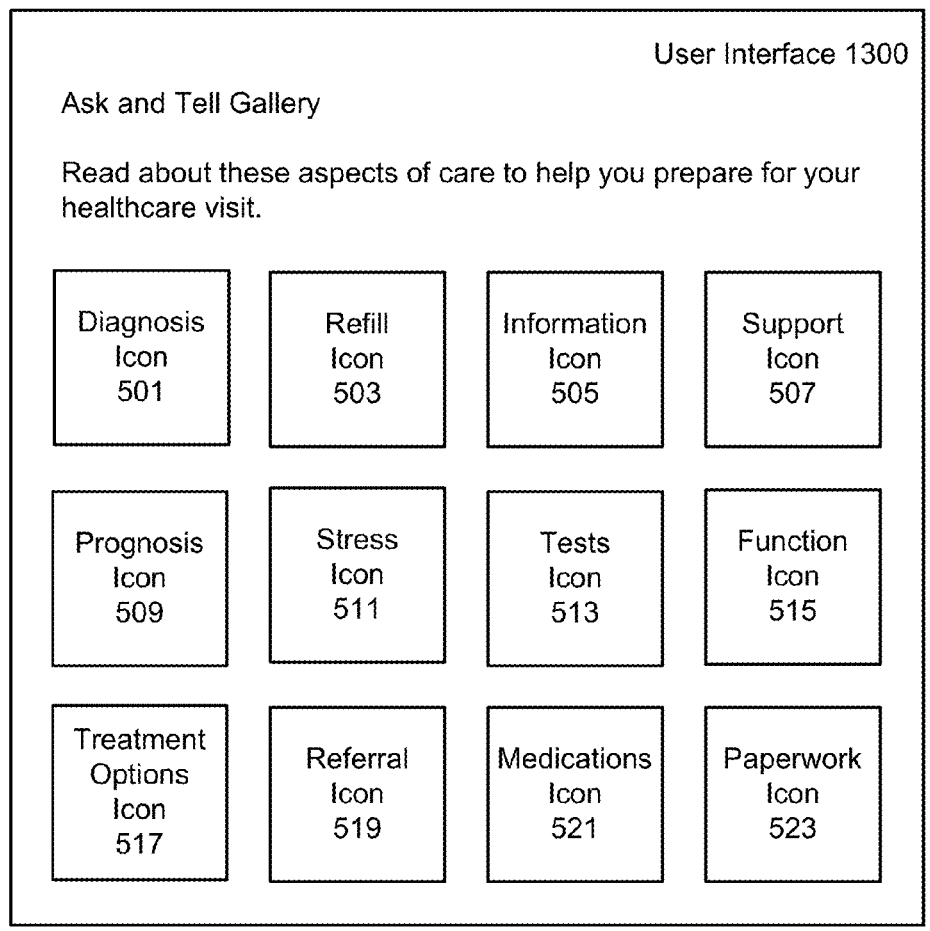
FIG. 13 illustrates a UI configured to allow parallel browsing access to an IPED.

With reference to a PICT, FIG. 3-FIG. 10 illustrate example UI which may be provided by PICT modules 246, FIG. 11 illustrates an example report that may be generated by PICT modules 246, and FIG. 12 illustrates an example PICT method. In general, a PICT may be implemented in part via PICT modules 246 and PICT data 286, optionally in conjunction with IPED modules 247 and IPED data 287, as described herein. The PICT modules 246 and PICT data 286 may be configured to provide a series of UI configured to interact with a user, e.g., a patient, to collect patient health data 298. The UI and corresponding method steps may be configured, for example, to identify patient issues, assign a short description to each identified issue, educate the patient about available aspects of care, identify a patient's desired aspects of care for each issue, prioritize the patient issues, identify desired information channels, and provide a printable report comprising prioritized patient issues to be addressed, desired aspects of care, and desired information channels. PICT modules 246 may be configured according to a wide variety of available computer programming techniques and technologies to produce UI such as illustrated in FIG. 3-FIG. 10, and to generate a report such as illustrated in FIG. 11, which techniques and technologies are understood in the art and/or may be developed in the future, and this disclosure is not limited to any particular technique or technology.

The UI illustrated in FIG. 3-FIG. 10 may be configured to receive patient health data 298. Furthermore, the UI illustrated in FIG. 3-FIG. 10 may include selectable "BACK" and/or "NEXT" buttons, illustrated for example in FIG. 3. The "BACK" and/or "NEXT" buttons may allow a user to navigate to previous and/or subsequent UI. In some embodiments, patient health data 298 received via a UI may be recorded as it is entered by a user and/or in response to user selection of a "BACK" and/or "NEXT" button. The UI illustrated in FIG. 3-FIG. 10 may also include status bars, e.g., showing a percentage of completion within each UI as the user progresses through the PICT.

FIG. 3-FIG. 12 also illustrate an example patient information collection method, comprising displaying UI illustrated in one or more of FIG. 3-FIG. 10, receiving and recording any patient health data 298 entered into a displayed UI, then displaying another, different UI illustrated in one or more of FIG. 3-FIG. 10, receiving and recording patient health data 298 for the next UI, and so forth until all desired patient health data 298 is received, and/or generating a report such as illustrated in FIG. 11. Some embodiments may comprise displaying any of the illustrated UI, plus any other UI as may be further included, in any desired order. Some embodiments may consist of only the UI provided herein, or any subset thereof. Furthermore, some embodiments may consist of only the UI provided herein, configured in one or more of the specific sequences of UI designated herein.

FIG. 3 illustrates a UI 300 provided by example PICT module(s) configured to identify patient issues. FIG. 3 also illustrates an example step in a patient information collection method. The UI 300 may comprise a plurality of fields 301, 302, 303. The fields 301, 302, 303 may accept user-entered data, e.g. descriptions of patient healthcare issues which a patient desires a healthcare provider to address. The UI 300, as well as all of the UI illustrated in FIG. 3-FIG. 9, as described above, may include "BACK" and/or "NEXT" buttons, allowing a user to navigate to previous and/or subsequent UI, and causing entered patient health data 298, such as entered descriptions of patient healthcare issues, to be stored.

FIG. 4 illustrates UI 400 provided by example PICT module(s) configured to assign a short description to one or more identified patient issues. FIG. 4 also illustrates an example step in a patient information collection method. The UI 400 may comprise one or more fields such as field 401, corresponding to one or more patient issues identified via FIG. 3. The field 401 may be configured for user entry of data, e.g. short descriptions corresponding to one or more patient issues identified via FIG. 3. Also, FIG. 4 may be automatically generated using patient health data 298 received via UI 300, such as patient health data received via field 301.

FIG. 5 illustrates UI 500 provided by example PICT module(s) configured to identify a patient's desired aspects of care corresponding to one or more identified patient issues, as well as to access an IPED configured to educate the patient about available aspects of care. FIG. 5 also illustrates an example step in a patient information collection method. The UI 500 may comprise a plurality of UI controls configured to receive aspect of care selections, comprising, for example, a selectable diagnosis control 502, a selectable information control 506, a selectable prognosis control 510, a selectable tests control 514, a selectable treatment options control 518, a selectable medications control 522, a selectable refill control 504, a selectable support control 508, a selectable stress control 512, a selectable function control 516, a selectable referral control 520, and a selectable paperwork control 524. Each of the above UI controls may be linked to an IPED, e.g., via linked IPED icons 501, 503, 505, 507, 509, 511, 513, 515, 517, 519, 521, and 523, which may be placed proximal to a corresponding UI control. The linked IPED icons may be configured to provide real-time user access to descriptions of corresponding aspects of care, from within a PICT. In some embodiments, UI 500 may comprise selectable field 530 configured to receive a free-form user entry of a desired aspect of care. Parallel access to the IPED may also be provided, as described below in connection with FIG. 13.

In some embodiments, UI 500 may include aspects of UI 400. A UI 500 may comprise both a field 401 for user entry of a short description corresponding to one or more patient issues identified via FIG. 3, and a plurality of selectable aspects of care which may be designated for the patient issue identified in the short description field 401. A method comprising a display of a UI 500 including a field 401 may omit displaying the UI 400.

In some embodiments, UI according to FIG. 4 and/or FIG. 5 may be presented repetitively for each patient issue identified via FIG. 3. In other words, once the user completes a short description and desired aspects of care for a patient issue identified via FIG. 3, the patient may be provided additional UI allowing for entry of additional short descriptions and desired aspects of care for additional patient issues identified via FIG. 3, until short descriptions and desired aspects of care are entered for all patient issues identified via FIG. 3.

Figure 6:
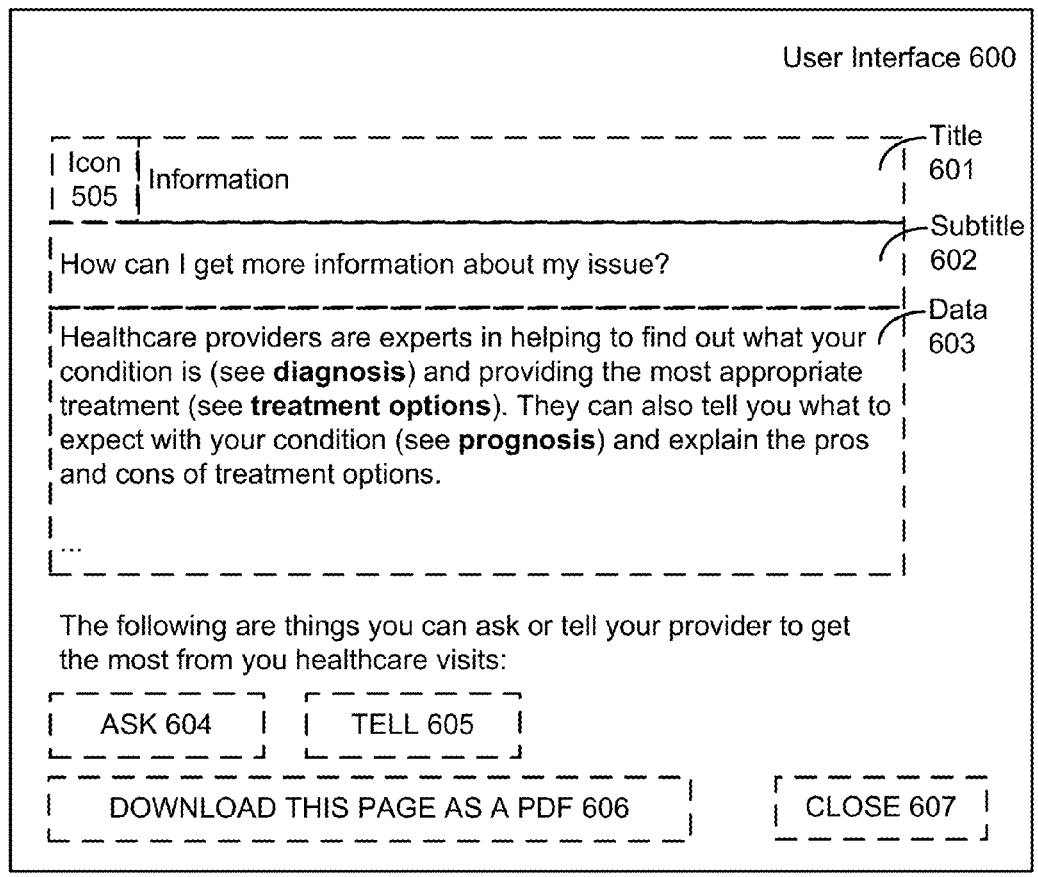
FIG. 6 illustrates a UI provided by example PICT module(s) configured to access an IPED.

FIG. 6 illustrates a UI 600 provided by example PICT module(s) configured to access an IPED. FIG. 6 also illustrates an example step in a patient information collection method. The UI 600 may be configured to provide IPED data, in response to a user selection of a linked IPED icon such as 505 in FIG. 5. The UI 600 may comprise, for example, a title 601, subtitle 602, data 603, an ask control 604, a tell control 605, a download page control 606, and a close control 607. The UI 600 may also comprise any further information, such as suggestions for things to do and quotes/examples of common concerns other patients might also have, to help patients normalize their experience and not feel stigma associated with many medical conditions, help patients with questions they may have about these conditions, and/or help with questions patients may want to ask or information they may want to convey to their healthcare providers about these conditions.

The ask control 604 may be configured to access further IPED data, comprising one or more useful questions to ask a healthcare provider, wherein the questions may be related to the aspect of care identified in a title such as 601. The UI 600 may be configured to provide a UI such as UI 1400, illustrated in FIG. 14, in response to receiving a selection of the ask control 604. The UI 1400 may be configured to generate an output comprising ask and/or tell selections as illustrated in FIG. 15.

The tell control 605 may be configured to access further IPED data, comprising one or more useful information items to tell a healthcare provider, wherein the information items may be related to the aspect of care identified in the title 601. The UI 600 may be configured to provide a UI such as UI 1400, illustrated in FIG. 14, in response to receiving a selection of the tell control 605. The UI 1400 may be configured to generate an output comprising ask and/or tell selections as illustrated in FIG. 15.

The download page control 606 may be configured to download the data from UI 600 in any file format, e.g., Portable Document Format (PDF), for digital storage. The close control 607 may be configured to close the UI 600 and may optionally return the user to the UI 500. In some embodiments, a UI such as 500 may be configured to pop-up or otherwise display a UI 600 in a foreground, over a background comprising UI 500, allowing the user to visually identify the possibility of returning to the UI 500 while viewing the UI 600.

FIG. 7 illustrates UI 700 provided by example PICT module(s) configured to provide a redundant opportunity to identify patient issues. FIG. 7 also illustrates an example step in a patient information collection method. The UI 700 may comprise a field 701 for entry of data comprising an additional patient healthcare issue which the user desires a healthcare provider to address. The UI 700 thereby provides another opportunity to enter a patient issue, after the user has had an opportunity to consider the first patient issues identified via FIG. 3, as well as consider short descriptions and desired aspects of care for the first issues via FIG. 4 and/or FIG. 5.

If patient health data 298 is received via field 701 in FIG. 7, then selection of the "NEXT" button may initiate a repetition of UI 400 and/or UI 500, to allow for entering short descriptions and desired aspects of care corresponding to an additional identified patient issue. If patient health data is not received via FIG. 7, then selection of the "NEXT" button may initiate loading of a UI such as illustrated in FIG. 8. Thus, in some embodiments, a "NEXT" button in the UI 700, and/or a configuration of a computing device configured to respond to selection of a "NEXT" button, may be dynamically reconfigured, in real time, to direct a user to an appropriate next UI for implementing the method described herein. Dynamic reconfiguration may occur for example in FIG. 7 as well as FIG. 5, in which a "NEXT" button may dynamically reconfigure to direct a user to either (a) another UI 500 according to FIG. 5, configured to receive aspect of care selections for another patient issue identified in FIG. 3, or (b) a UI 700 configured to receive patient health data 298 comprising an additional identified patient issue, or (c) in embodiments not utilizing UI 700 according to FIG. 7, a UI according to FIG. 8.

FIG. 8 illustrates a UI 800 provided by example PICT module(s) configured to prioritize patient issues. FIG. 8 also illustrates an example step in a patient information collection method. The UI 800 may comprise one or more priority positions, e.g., 801 and 802, and priority controls, e.g., 811 and 812 identifying patient health issues, e.g., using the patient issues received via FIG. 3 and/or short descriptions of patient health issues received via FIG. 4 and/or FIG. 5. The priority controls 811 and 812 may be automatically generated in UI 800 using data from previous UI 300, 400, and/or 500. The UI 800 may be configured to allow dynamic repositioning of the priority controls 811 and 812 into priority positions 801 and/or 802. For example, a user may select a priority control 811 and drag the priority control 811 to a desired priority position 801 or 802. Dropping a priority control 811 into a priority position 801 may cause each of the other priority controls, e.g., priority control 812 that may occupy a same or lower priority position to move down one priority position. If a priority control 811 is moved out of a top priority position 801, then dropping a priority control 811 into a priority position 802 may cause each of the other priority controls, e.g., priority control 812 that may occupy a same or higher priority position to move up one priority position. In some embodiments, when only one patient issue is identified via FIG. 3, FIG. 8 may be omitted, for example by displaying the UI 900 of FIG. 9 immediately after a UI 700 of FIG. 7, when the user chooses not to enter data into UI 700.

In some embodiments, UI 800 may employ color to assist with patient issue prioritization. For example, selecting a priority control may cause the priority control to change color, and dragging the selected priority control over a second priority control may cause the second priority control to change color, signaling to the user that dropping a selected priority control will cause the priority control to take the priority position of the second priority control. Also, in some embodiments, UI 800 may be configured to display a partially transparent "ghost" image of a selected priority control when moving the selected priority control to another priority position. Hitting a "NEXT" button may finalize the user's prioritization of the various identified patient health issues for the purpose of generating a report.

FIG. 9 illustrates a UI 900 provided by example PICT module(s) configured to identify desired information channels. FIG. 9 also illustrates an example step in a patient information collection method. The UI 900 may comprise a plurality of selectable information channel identifications 901-913. The information channel identifications may comprise, for example, a verbal instructions channel 901, a figures or graphs channel 903, an audio taping of my visits channel 905, a taking notes channel 907, a web-based information channel 909, an interacting in groups channel 911, a written instructions channel 902, an information pamphlets channel 904, a getting an opportunity to ask questions channel 906, a getting emailed information channel 908, an audiovisual materials channel 910, a bringing someone to the visit with me channel 912, and an "other" channel comprising a field 920 configured to receive a free-form user identification of a desired information channel.

Some embodiments may be configured to leverage data entered via free-form fields such as field 920, field 530, field 1401, and/or field 1402 for tool (e.g., PICT, IPED or COP-ICT) upgrade. For example, data entered in free-form fields may be compiled for the purpose of tool upgrades, as well as stored with patient health data 298. Data for use in tool upgrades may or may not be stored in a same location as patient health data 298. Data for use in tool upgrades may be classified, e.g., by an upgrade module included in modules and data 280, to determine patterns and common requests. For example, an upgrade module may be configured to classify data for use in tool upgrades by keyword(s). The upgrade module may generate administrator keyword alerts when a threshold number of requests comprising a particular keyword are received. An upgrade module may be configured to produce keyword reports showing the keywords used to classify the data for use in tool upgrades, and numbers of requests corresponding to each keyword. Data for use in tool upgrades, keyword alerts, and/or keyword reports may be used to upgrade the selectable controls for a tool, e.g., by including a new selectable information channel in UI 900 reflecting a commonly requested information channel in field 920, by including a new selectable aspect of care in UI 500 reflecting a commonly requested aspect of care in field 530, by including a new question in UI 1400 reflecting a common question in field 1401, and/or by including a new information item in UI 1400 reflecting a commonly received free-form information item in field 1402.

In some embodiments, an upgrade module may also be configured to indicate, e.g. in a backend report as described herein, frequencies of occurrence of free-form entries of aspects of care (field 530), ways of receiving health information (field 920), questions to ask healthcare providers (field 1401) or information items to tell their healthcare providers (field 1402). Free-form entries of aspects of care (field 530) that are sufficiently frequent and sufficiently distinct from selectable aspects of care (for example, a selectable diagnosis control 502, a selectable information control 506, a selectable prognosis control 510, a selectable tests control 514, a selectable treatment options control 518, a selectable medications control 522, a selectable refill control 504, a selectable support control 508, a selectable stress control 512, a selectable function control 516, a selectable referral control 520, and a selectable paperwork control 524) may be integrated to become selectable aspects of care in subsequent, upgraded versions of the tool, or may comprise selectable aspects of care in tailored modifications for use with certain populations of patient users. Free-form entries of ways of receiving health information (field 920) that are sufficiently frequent and sufficiently distinct from selectable ways of receiving health information (for example, a verbal instructions channel 901, a figures or graphs channel 903, an audio taping of my visits channel 905, a taking notes channel 907, a web-based information channel 909, an interacting in groups channel 911, a written instructions channel 902, an information pamphlets channel 904, a getting an opportunity to ask questions channel 906, a getting emailed information channel 908, an audio-visual materials channel 910, a bringing someone to the visit with me channel 912) may be integrated to become selectable ways of receiving health information in subsequent, upgraded versions of the tool, or may comprise selectable ways of receiving health information in tailored modifications for use with certain populations of patient users. Questions to ask healthcare providers (field 1401) or information items to tell their healthcare providers (field 1402) that are sufficiently frequent and sufficiently distinct from selectable questions to ask healthcare providers or selectable information items to tell their healthcare providers, may be integrated to become selectable questions to ask healthcare providers or selectable information items to tell healthcare providers in subsequent, upgraded versions of the tool, or may comprise selectable questions to ask healthcare providers or selectable information items to tell healthcare providers for certain populations of patient users.

Figure 10:
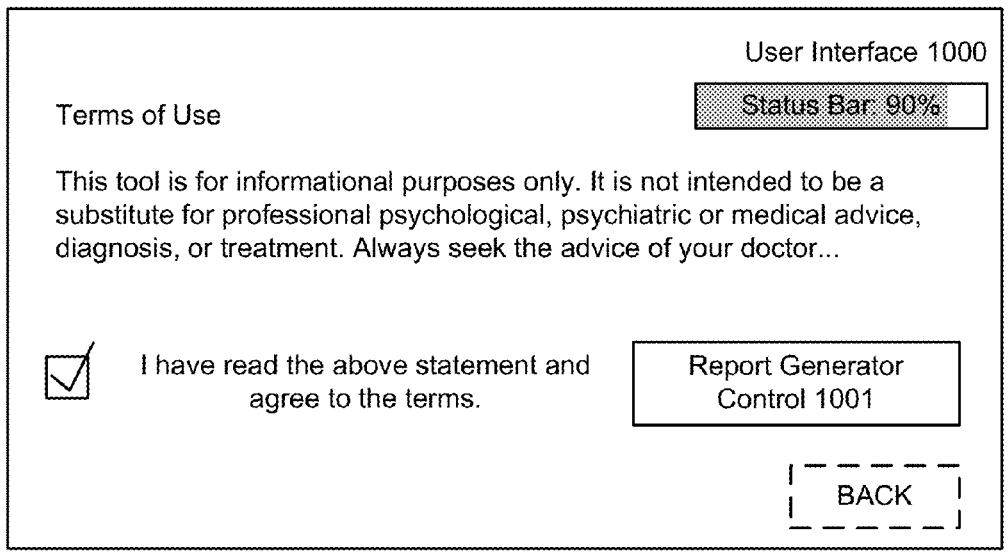
FIG. 10 illustrates a UI provided by example PICT module(s) configured to provide a printable summary comprising prioritized patient issues to be addressed, desired aspects of care, and desired information channels.

FIG. 10 illustrates a UI 1000 provided by example PICT module(s) configured to provide a printable report comprising prioritized patient issues to be addressed, desired aspects of care, and desired information channels. FIG. 10 also illustrates an example step in a patient information collection method. The UI 1000 may comprise a checkbox for agreeing to contractual terms, and a report generator control 1001 configured to initiate generation of a printable report. It will be appreciated that UI configured similar to UI 1000 may also be provided in connection with the IPED and COPICT disclosed herein.

FIG. 11 illustrates an example report 1100 as may be generated by PICT modules. FIG. 11 also illustrates an example step in a patient information collection method. A PICT may be configured to display a report 1100 in response to receiving a report generation command via report generator control 1001. Alternatively, a PICT may be configured to generate and download a report 1100 to a client computing device, e.g., as a Portable Document Format (PDF) file, or other file type as appropriate, in response to receiving a report generation command via report generator control 1001. The report 1100 may comprise the patient health data 298 received via UI 300, 400, 500, 700, 800, and/or 900. The patient health data 298 may be arranged for example by providing each patient health issue identified in FIG. 3 and/or FIG. 7 together with desired aspects of care for that issue, as selected via UI 500. Desired information channels as selected via UI 900 may be provided in an additional section of the report 1100.

The report 1100 comprises field 1111, field 1112, field 1121, field 1131, field 1141, field 1151, field 1161, field 1171, and field 1182, as well as various explanatory text and instructions as shown. Field 1111 may comprise a Patient ID. In some embodiments, the Patient ID may be a patient name, or Patient ID number such as a social security number, medical record number, or other identifier. In some embodiments, the Patient ID may be left blank, allowing the patient to write in the Patient ID. For example, some embodiments may avoid collecting Patient ID information to preserve patient privacy.

Field 1112 may comprise a Date 2. Date 2 may comprise a date of a scheduled healthcare visit. This information may be collected for example by adding a Date 2 field to any of the UI disclosed herein, or by providing a separate UI configured to receive healthcare visit schedule information. As with Patient ID, the Date 2 may also be left blank, allowing the patient to write in the visit date.

Field 1121 may comprise a Date 1. Date 1 may comprise a date of report generation. In some embodiments, a report generator module may be configured to retrieve date information from a computer that executes the report generator module, at the time of generating the report 1100, and may be configured to populate the Date 1 field with retrieved date information. If the time elapsed between Date 1 and Date 2 is significant, the clinician may determine that the patient needs to complete another PICT, since the issues raised in generation of the output in report 1100 may not be sufficiently current.

Field 1131 may comprise a field 301 (or 401) and a field 1132 comprising corresponding selected aspects of care. For example, field 1131 may identify a patient health issue, using patient health data 298 received via field 301. In embodiments allowing entry of short descriptions, the short description received for example via field 401 may be used within field 1131. Field 1131 may also comprise field 1132, configured to identify selected aspects of care corresponding to the patient health data 298 received via field 301, and received by the PICT via UI 500. Field 1131 may also comprise a "notes" section configured for entry of user notes relating to the identified patient health issue.

Field 1141, 1151, 1161, and 1171 may be configured similarly to field 1131. That is, field 1141 may comprise a field 302 and a field 1142 comprising corresponding selected aspects of care, field 1151 may comprise a field 303 and a field 1152 comprising corresponding selected aspects of care, field 1161 may comprise a field 3XX (an example additional field in UI 300) and a field 1162 comprising corresponding selected aspects of care, field 1171 may comprise a field 3XY (an example additional field in UI 300) and a field 1172 comprising corresponding selected aspects of care, and field 1182 may comprise selected information channels received via UI 900.

In some embodiments, PICT module(s) may be configured to automatically generate two or more identical copies of a report, to ensure that each participant—the patient and the healthcare provider, has one during a patient visit to a healthcare provider. Also, a report 1100 may be limited to one page in size, to increase the likelihood, for example, that information by being on separate pages is not separated or lost or does not appear overwhelming to the busy clinician. In some embodiments, a number of fields for report 1100 may be restricted, or formatting and font size may be adjusted to limit report output to one page.

In some embodiments, PICT module(s) may be configured to generate a report comprising a section for "main issues" and/or a section for "remaining issues". Identification of main issues may help set expectations about the issues that can reasonably be addressed during a patient visit to a healthcare provider. The main issues may comprise a subset of the identified patient issues corresponding to the highest priority patient issues. In some embodiments, the main issues may be limited to a select number, e.g., the top two priority patient issues. Reports may be configured with larger fields for main issues. For example, FIG. 11 illustrates larger fields for the main issues on the left side of the report. Larger fields may comprise for example desired aspects of care and notes sections.

Remaining issues may be listed in smaller fields in a different section of the report, e.g., the right side as illustrated in FIG. 11. The smaller fields may include less information, for example by including only an identification of a patient issue, or may be provided in smaller font, or may be otherwise made visually less prominent that the main issues. Inclusion of remaining issues in a report reminds parties to a healthcare visit of outstanding issues to be addressed if there is enough time in a visit, or for follow up in a next visit. The listing of remaining issues also provides a fail-safe so that if the patient ranks an issue lower than a provider might triage it (e.g. chest pain), the provider can still be aware of the issue. The listing of remaining issues also allows providers to address issues such as refills or paperwork which, while lower priority, can nonetheless be conveniently addressed for example by a nurse or medical assistant preparing a prescription slip or collecting paperwork to complete sections for the doctor or other healthcare provider.

In some embodiments, PICT module(s) may be configured to generate notes sections in reports such as FIG. 11. Notes sections may be generated for example to ensure that the provider can make notes for the patient in a number of places. The patient may similarly make personal notes on the patient copy of the report. In some embodiments, a PICT or website providing a PICT may be configured to provide a report similar to report 1100, in which the fields are left empty, for parallel access, along with a PICT as described herein. A server may be configured to host a website comprising a downloadable "empty" report, as well as the various other UI described herein. The downloadable report may be accessible from within the context of a PICT or via another related webpage. Clinics may also use paper versions of PICT, IPED, and COPICT tools that can be created as a carbon copy allowing patients to complete the form and have two copies—one for the clinician and one for themselves.

FIG. 12 illustrates an example patient information collection method that may be performed in connection with a PICT as provided herein. The method comprises identifying patient issue(s) 1201, for each issue, identifying aspects of care 1202, prioritizing issues 1203, identifying information preferences 1204, and generating a report 1205. It will be appreciated that each of the illustrated method steps may be modified in accordance with the discussion of the various PICT UI provided herein. For example, identifying patient issue(s) 1201 may comprise providing a UI comprising a plurality of fields for identifying patient issues, and receiving one or more identifications of patient issues. Identifying aspects of care 1202 may comprise, for each received patient issue, providing a UI comprising a set of selectable aspects of care, and further comprising links to an IPED including educational information regarding the selectable aspects of care, and receiving aspect of care selections for each received patient issue. Prioritizing issues 1203 may comprise providing a UI for prioritizing received patient issues, and receiving patient issue prioritizations. Identifying information preferences 1204 may comprise providing a UI comprising a set of selectable information channels, and receiving information channel selections. Generating a report 1205 may comprise generating a report comprising prioritized identifications of patient issues along with selected aspects of care corresponding to each patient issue.

FIG. 13 illustrates UI 1300 configured to allow parallel browsing access to an IPED. IPED modules 247 and data 287 may be configured to generate a UI such as 1300. UI 1300 may comprise a plurality of linked IPED icons, e.g. a diagnosis icon 501, a refill icon 503, a information icon 505, a support icon 507, a prognosis icon 509, a stress icon 511, a tests icon 513, a function icon 515, a treatment options icon 517, a referral icon 519, a medications icon 521, and a paperwork icon 523, introduced above with reference to FIG. 5. The linked IPED icons may represent aspects of care such as those available from UI 500. Each of the linked IPED icons may be linked to data from an IPED. The UI 1300 may be configured to receive a linked IPED icon selection, and to provide IPED data corresponding to the received selection. For example, UI 1300 may be configured to provide a UI such as 600 in response to receiving a selection of information icon 505. In some embodiments, UI such as UI 600 provided in response to selection of each linked IPED icon 501, 503, 505, 507, 509, 511, 513, 515, 517, 519, 521, and/or 523, may comprise ask and tell controls such as 604 and 605, configured to access a UI such as illustrated in FIG. 14.

FIG. 14 illustrates UI 1400 as may be provided in response to selection of an ask control 604 and/or tell control 605 from an IPED UI such as 600. IPED modules 247 and data 287 may be configured to generate a UI such as 1400. FIG. 14 comprises a plurality of selectable questions in an "ask" category including a selectable field 1401 configured for free-form entry of a patient question, a plurality of selectable information items in a "tell" category including a selectable field 1402 configured for free-form entry of an information item, and a view/print selections control 1403. The UI 1400 may be configured to compile selected questions and/or informational items from UI 1400 into an output UI 1500, and/or to generate a file configured for viewing, printing and/or saving of the compiled selected questions.

FIG. 15 illustrates UI 1500 as may be provided in response to receiving a view/print selections command via view/print selections control 1403 in UI 1400. IPED modules 247 and data 287 may be configured to generate a UI such as 1500. The UI 1500 may also be configured as a viewable and/or downloadable report, which may be electronically viewed and/or sent to any destination as convenient, for example, may be sent as an email, text, or other electronic communication to a healthcare provider, patient, or clinic device allowing convenient access to the information included in UI 1500 during a healthcare visit. FIG. 15 includes a sample set of selections corresponding to an example set of selections from FIG. 14, corresponding to an example set of self-identified patient needs.

In some embodiments, IPED modules 247 and data 287 may be configured to store selections received via UI 1300 and UI 1400 as patient health data 298, which may be used for example by backend reporting modules to understand prevailing areas of patient uncertainty and/or educational interest.

Figure 16:
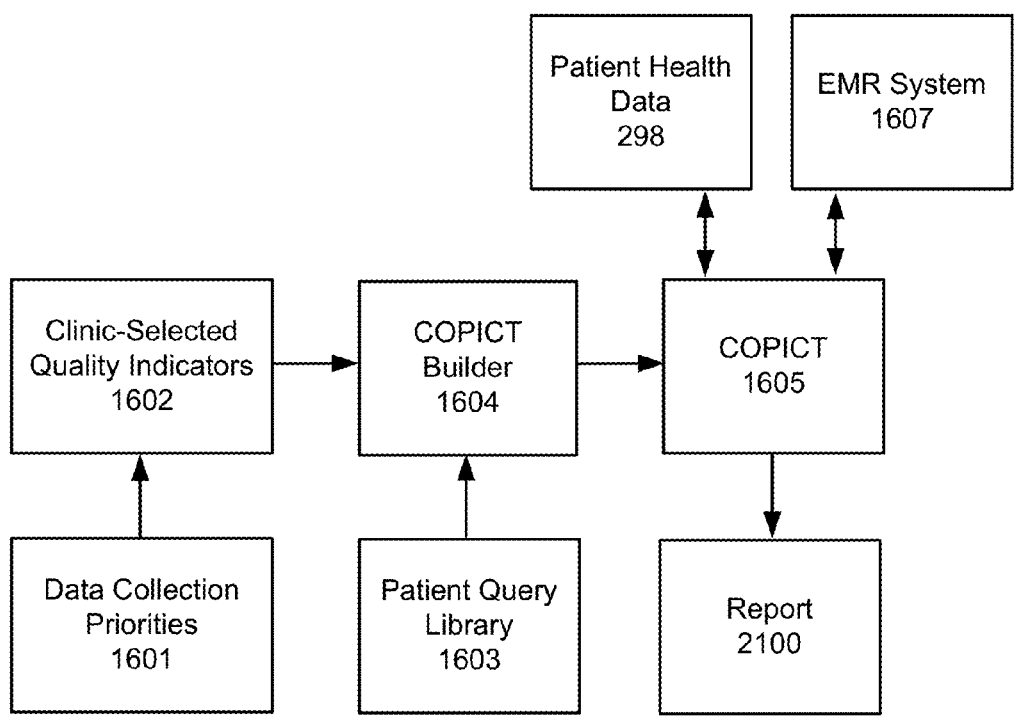
FIG. 16 is a block diagram illustrating example components of a COPICT and corresponding methods.

FIG. 16 illustrates components of a system and corresponding method that may be performed in connection with a COPICT. FIG. 16 comprises a data collection priorities block 1601, a clinic selected quality indicators block 1602, a patient query library block 1603, a COPICT builder block 1604, a COPICT block 1605, a patient health data block 298, an EMR system block 1607, and a report block 2100.

In FIG. 16, data collection priorities 1601 may be used, at least in part, to determine clinic selected quality indicators 1602. Data collection priorities 1601 may for example comprise healthcare service quality indicators selected by one or more government agencies such as CMS, state level agencies, local (city or regional) agencies, private healthcare information collection agencies, insurance companies, and/or any organization measuring performance of an overall healthcare system as well as specific clinics. Clinic selected quality indicators 1602 may comprise clinic-selected areas of health priority, which in some embodiments may be selected from among the data collection priorities 1601 and may comprise, e.g., guideline-level quality indicators such as colon cancer screening and glaucoma testing, as selected to suit the measurement priorities of a specific clinical setting. Clinics and healthcare organizations may have different data collection priorities, depending on what type of services are provided, geographical region, demographics of the clinic patients, federal, state, and local policies and priorities. Data collection priorities 1601 that apply to a clinic may be selected by the clinic as clinic selected quality indicators 1602, that is, information that the clinic wishes to know about its patients.

COPICT builder 1604 may be configured to use clinic selected quality indicators 1602 along with patient query library 1603 to build a COPICT 1605. COPICT builder 1604 and patient query library 1603 thereby allow building of custom COPICT 1605 to suit the needs of different clinics, as well as the changing needs of individual clinics. In some embodiments, a COPICT builder 1604 and patient query library 1603 may be configured to include multiple patient query options for a given quality indicator, allowing for individualization of patient queries included in a COPICT 1605 based on the unique characteristics of the clinic/organization or patient population characteristics. Also, the COPICT builder 1604 may be configured to allow modifications to patient query library 1603, and the patient queries included therein, to accommodate changes in clinic populations/circumstances over time.

A COPICT 1605 may be configured to receive (e.g., from a patient) and store patient health data 298, and may also share patient health data 298 with EMR system 1607. COPICT 1605 may be configured to generate a report 2100 comprising the patient health data 298 collected in accordance with the desired clinic selected quality indicators 1602.

In some embodiments, elements of FIG. 16 may be implemented via a computing apparatus such as illustrated in FIG. 2. For example, COPICT builder 1604 may be implemented via COPICT builder modules 295 and COPICT builder data 296. COPICT builder data 296 may comprise a patient query library 1603. COPICT 1605 may be implemented via COPICT modules 248 and COPICT data 288, wherein COPICT data 288 may comprise patient queries selected from a patient query library 1603. COPICT 1605 may be configured to store received data as patient health data 298, and to use the stored patient health data 298 to generate report 2100. EMR system 1607 may be implemented via EMR integration modules 293 and EMR data 294.

In some embodiments, clinic oriented patient information collection methods may be carried out in connection with FIG. 16. Example clinic oriented patient information collection methods may comprise maintaining a library of patient queries 1603, wherein each patient query is designed to retrieve patient health data, receiving a clinic selected quality indicators 1602, and/or building a COPICT 1605 comprising patient queries from the library of patient queries 1603 corresponding to the clinic selected quality indicators 1602 and fields configured to receive patient health data 298 in response to the patient queries. In some embodiments, clinic oriented patient information collection methods may further comprise providing the COPICT 1605 to one or more clinic patients; receiving and storing patient health data 298 via fields configured to receive patient health data 298; generating a report 2100 comprising received patient health data 298; electronically transmitting the report 2100 to one or more of a clinic, a clinic patient, and a clinic healthcare provider; sharing patient health data between the COPICT 1605 and the EMR management system 1607; providing an administrator interface configured to receive an identification of a clinic patient; receiving an identification of a clinic patient via the administrator interface, and/or providing a COPICT configured to retrieve patient health data for the identified clinic patient.

The COPICT builder may be fully or partially automated. In some embodiments, one or more clinic selected quality indicators 1602 may be provided, for example as a data file, to an operator of the COPICT builder 1604. The operator may use the clinic selected quality indicators 1602 to select and combine patient queries from the patient query library 1603, to generate the COPICT 1605 comprising patient queries configured to retrieve patient health data that matches the clinic selected quality indicators 1602. In some embodiments, the COPICT builder 1604 may be configured to receive the clinic selected quality indicators 1602, and to automatically select and combine corresponding patient queries from the patient query library 1603 to generate the COPICT 1605. Patient queries in the patient query library 1603 may be configured with response fields that receive patient health data, as well as information sections as illustrated herein, or the response fields and information sections may be maintained separately from the patient queries and combined with queries during COPICT build.

In some embodiments, the COPICT 1605 may be configured to generate a report 2100 comprising patient health data 298 received at the COPICT 1605 in response to patient queries included in the COPICT 1605. The patient health data 298 may be received, for example, via an online series of UI provided by the COPICT which may be completed from a patient's client computer, smart phone, or other device accessing a clinic or other server configured to host a website comprising the COPICT. In some embodiments, the patient health data 298 may be received at least in part from an EMR system 1607. The patient health data 298 may also be received for example via a paper questionnaire based on a COPICT that can be mailed or distributed in a clinic waiting room, and/or via a paper questionnaire based on a COPICT that is printed from a PDF (or other file type) downloaded from a clinic website. As discussed above, patient health data 298 may also be received via other data transmissions such as text message or instant message.

FIG. 17-FIG. 20 illustrate example UI as may be included in a COPICT 1605. Each of the UI in FIG. 17-FIG. 20 may comprise a patient query designed to retrieve patient health data. Each of the UI in FIG. 17-FIG. 20 may be included in a COPICT 1605, if the data that the patient query gathers is specified in a desired clinic selected quality indicators 1602. A COPICT builder 1604 may be configured to build one or more COPICTS 1605 comprising UI such as illustrated in FIG. 17-FIG. 20.

FIG. 17 illustrates a UI 1700 comprising an example patient query 1701, response fields 1702, and information section 1703. The information section 1703 includes image 1704.

Figure 18:
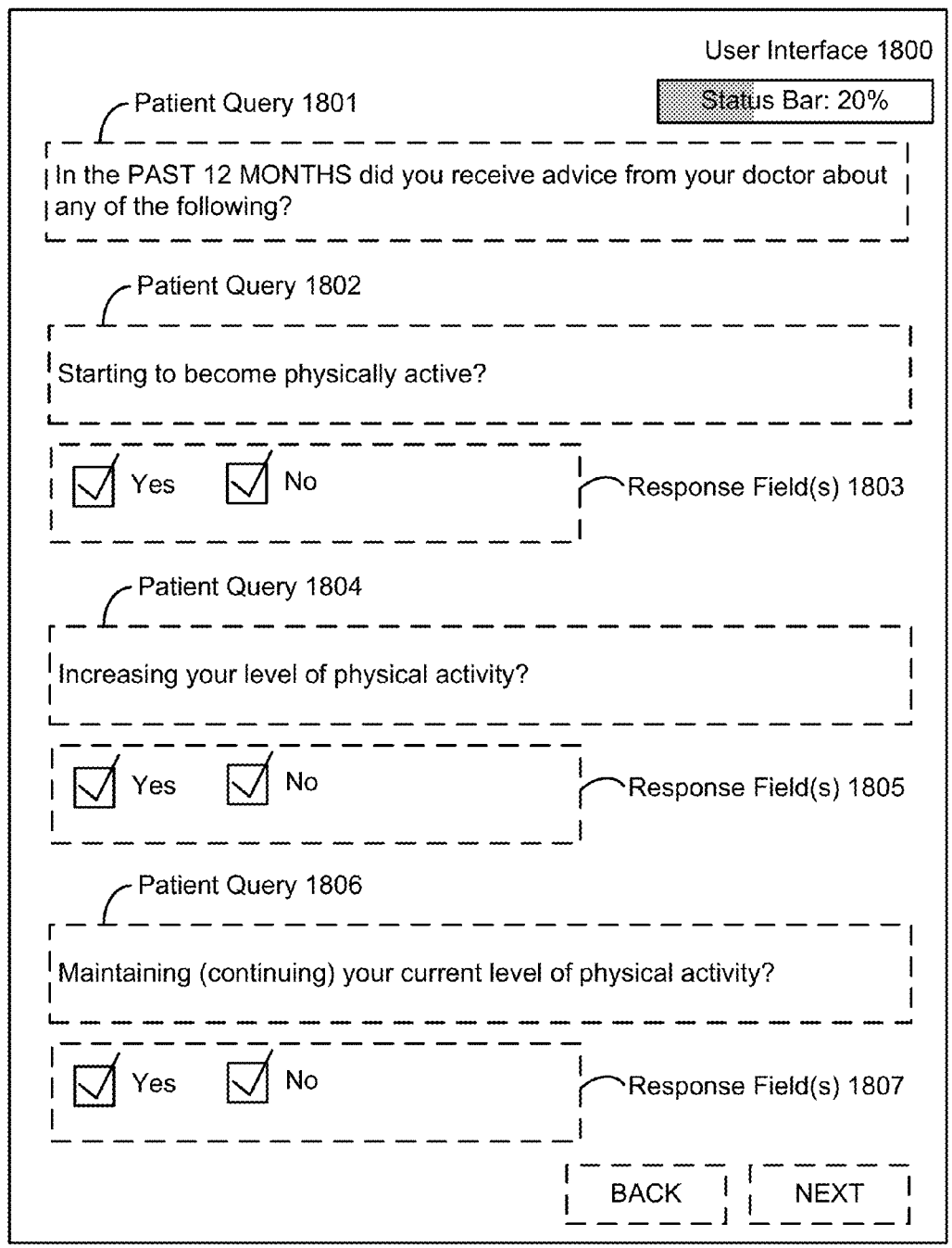
FIG. 18 illustrates an example UI as may be included in a COPICT.

FIG. 18 illustrates a UI 1800 comprising an example patient query 1801 including multiple sub-queries 1802, 1804, and 1806. Each sub-query has a corresponding response field 1803, 1805, and 1807 respectively.

Figure 19:
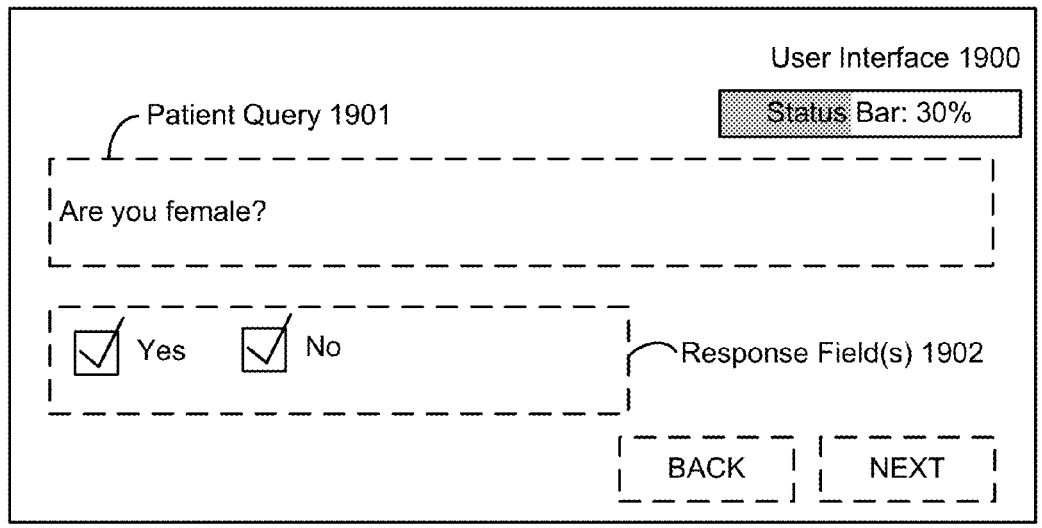
FIG. 19 illustrates an example UI as may be included in a COPICT.
Figure 20:
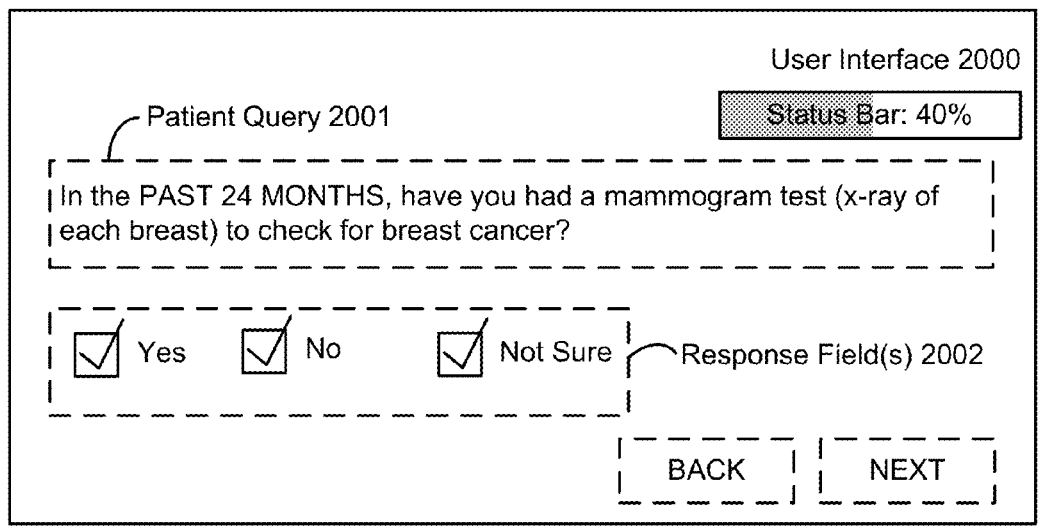
FIG. 20 illustrates an example UI as may be included in a COPICT.

FIG. 19 illustrates a UI 1900 comprising an example patient query 1901 configured as a conditional query. For example, if "Yes" is selected in the response field 1902, a COPICT 1605 may be configured to apply one or more subsequent queries, such as illustrated in FIG. 20. If "No" is selected in the response field 1902, a COPICT 1605 may be configured to skip one or more subsequent queries, such skipping the query illustrated in FIG. 20.

FIG. 20 illustrates a UI 2000 comprising an example patient query 2001 following a UI 1900 comprising a conditional query 1901. UI 2000 comprises response fields 2002. A COPICT may be configured to display or not display UI 2000, based on data received through a UI 1900 comprising a conditional query 1901.

FIG. 21 illustrates an example report 2100 as may be generated by COPICT modules 248. FIG. 21 also illustrates an example step in a clinic oriented patient information collection method. A COPICT may be configured to display a report 2100 in response to receiving a report generation command via report generator control available in a COPICT UI, e.g., a report generator control similar to 1001. Alternatively, a COPICT may be configured to generate and download a report 2100 to a client computing device, e.g., as a Portable Document Format (PDF) file, or other file type as appropriate, in response to receiving a report generation command via a report generator control. The report 2100 may comprise the patient health data received via UI such as 1700, 1800, 1900 and/or 2000. The patient health data may be arranged for example by providing patient health data that is grouped into a plurality of content sections 2130, 2140, 2150.

The report 2100 comprises field 2111, field 2112, field 2121, one or more sections such as 2130, 2140, and 2150, as well as various explanatory text and instructions as shown. Each section such as 2130, 2140, and 2150 comprises one or more content elements, and each content element comprises one or more fields. For example, section 2130 comprises content element 2131, and content element 2131 comprises field 2132. Section 2140 comprises content elements 2141, 2142, which comprise fields 2144 and 2145, respectively. Section 2140 also comprises content element 2143, which comprises fields 2146 and 2147. Section 2150 comprises content element 2151, and content element 2151 comprises field 2152.

Field 2111 may comprise a Patient ID. In some embodiments, the Patient ID may be a patient name, or Patient ID number such as a social security number, medical record number, or other identifier. In some embodiments, the Patient ID may be left blank, allowing the patient to write in the Patient ID. For example, some embodiments may avoid collecting Patient ID information to preserve patient privacy.

Field 2112 may comprise a Date 2. Date 2 may comprise a date of a scheduled healthcare visit. This information may be collected for example by adding a Date 2 field to any of the UI disclosed herein, or by providing a separate UI configured to receive healthcare visit schedule information. As with Patient ID, the Date 2 may also be left blank, allowing the patient to write in the visit date.

Field 2121 may comprise a Date 1. Date 1 may comprise a date of report generation. In some embodiments, a report generator module may be configured to retrieve date information from a computer that executes the report generator module, at the time of generating the report 2100, and may be configured to populate the Date 1 field with retrieved date information.

COPICT modules 248 may be configured to generate a report 2100 by completing fields 2111, 2112, and/or 2121, determining a set of content elements for the report, setting field values for the field(s) included in each content element, and placing related content elements in sections.

In some embodiments, determining a set of content elements for the report 2100 may comprise determining a set of required content elements. COPICT modules 248 may for example be configured to consult a file listing required content elements for the report 2100. In some embodiments, determining a set of content elements for the report 2100 may comprise determining a set of relevant content elements. Relevant content elements may be determined based on patient health data received via the COPICT. For example, COPICT users may provide patient health data in response to some, but not all, COPICT UI. Relevant content elements may be those content elements corresponding to a COPICT UI for which a patient (or other COPICT user) provided a response.

A set of content elements may be retrieved from a content element library. The content element library may comprise text, formatting, and other data for display with a content element.

Field values for the field(s) included in each content element may be set for example according to patient health data received at the COPICT. For example, a "Yes", "No", or "Not Sure" response received in a COPICT UI field such as 1702, 1803, 1805, 1807, 1902, and/or 2002 may be used to set a corresponding content element field to "Yes", "No", or "Not Sure". "Not Applicable" is another possible field value that may be encountered, as are free-form text entries such as identifications of medications populating field 2146 in the example report 2100.

Placing related content elements in sections may be accomplished using any number of approaches. For example, each content element may comprise metadata identifying a section or sections to which it belongs, allowing grouping of content elements according to section(s) identified in content element metadata. It will be appreciated that any of a variety of approaches may be employed for organizing content elements into sections.

The report 2100 is one page in size. In some embodiments, a number of content elements for report 2100 may be restricted, or formatting and font size may be adjusted to restrict report output to one page. Also, as with generating a report for patient health data gathered via the PICT, generating a report for patient health data gathered via the COPICT may comprise automatically generating two copies of the report 2100 in some embodiments.

In addition to the reports described in connection with the PICT, IPED and COPICT, it will be appreciated that received patient health data 298 may be used to produce a variety of other useful reports. In some embodiments, a computer 200 may be configured with backend reporting modules 297 configured to generate one or more useful backend reports using aggregated patient health data 298 which is collected using PICT, IPED, and/or COPICT tools according to this disclosure.

For example, in some embodiments a server or other computing device 200 may be configured to provide a PICT, IPED, and/or COPICT. The PICT may comprise modules configured to provide UI as described herein, such as UI comprising a plurality of fields for identifying patient issues, UI comprising a set of selectable aspects of care for each identified patient issue; UI comprising a set of selectable information channels, and UI for initiating report generation for reports comprising the identifications of patient issues along with selected aspects of care corresponding to each patient issue, and further comprising the information channel selections. The IPED and/or COPICT may comprise IPED and/or COPICT modules, respectively, as also described herein.

The server may be configured to store collected patient health data, locally and/or in a database that may be hosted on one or more additional servers/computing devices. The patient health data may include any patient health data described herein, including but not limited to: patient issues received via a PICT UI comprising a plurality of fields for identifying patient issues; selected aspects of care received via a PICT UI comprising a set of selectable aspects of care; data received via a PICT field configured to receive free-form aspect of care descriptions; selected information channels received via a PICT UI comprising a set of selectable information channels; data received via a PICT field configured to receive free-form information channel descriptions; selected questions for a healthcare provider received via an IPED UI comprising a set of selectable questions; data received via an IPED field configured to receive free-form healthcare provider questions; selected information items for a healthcare provider received via an IPED UI comprising a set of selectable information items; data received via an IPED field configured to receive free-form information items for a healthcare provider; and/or data received via response fields such as 1702, 1803, 1805, 1807, 1902, and/or 2002 included in a COPICT.

In addition to the PICT, IPED, and/or COPICT modules, an example server may further comprise one or more backend reporting modules configured to generate one or more reports summarizing patient health data, e.g., in the case of the PICT, the patient health data received via the fields for identifying patient issues, selectable aspects of care, and selectable information channels.

In some embodiments, backend reporting modules 297 may be configured to generate reports comprising data corresponding to a single patient and/or multiple patients. For example, backend reporting modules 297 may be configured to identify a group of patients, and to generate reports using patient health data 298 from an identified group. Backend reporting modules 297 may be configured to allow patient grouping by clinic, healthcare provider or other shared healthcare professional serving the plurality of patients, and/or shared patient attributes such as patient age, patient gender, previous patient medical issues, patient geographical region of residence, or other patient attributes for which data may be available.

In some embodiments, backend reporting modules 297 may also be configured to generate reports comprising data corresponding to one or more sessions with a PICT, IPED, and/or COPICT. For example, backend reporting modules 297 may be configured to generate a multi-session report comprising patient health data received during a plurality of user sessions with PICT, IPED, and/or COPICT UI.

In some embodiments, backend reporting modules 297 may be configured to generate reports comprising patient problem rate indices corresponding to one or more patients. A patient problem rate index may comprise a number of issues a patient (or group of patients) brings up per unit of time, e.g., per year.

In some embodiments, backend reporting modules 297 may be configured to generate a report comprising occurrence rates of patient health data received via the PICT, IPED, and/or COPICT. For example, reports may comprise occurrence rates of patient issues received via the PICT UI comprising a plurality of fields for identifying patient issues. Reports may comprise occurrence rates of selected aspects of care received via the PICT UI comprising a set of selectable aspects of care. Reports may comprise occurrence rates of selected information channels received via the PICT UI comprising a set of selectable information channels. Reports may comprise occurrence rates of selected questions for a healthcare provider received via an IPED UI comprising a set of selectable questions. Reports may comprise occurrence rates of selected information items for a healthcare provider received via an IPED UI comprising a set of selectable information items. Reports may comprise occurrence rates of patient health data received via free-form entry fields such as fields 530, 920, 1401 and/or 1402, e.g., occurrence rates of free-form responses that include one or more designated keywords. Reports may comprise occurrence rates of patient health data received via response fields such as 1702, 1803, 1805, 1807, 1902, and/or 2002 included in a COPICT.

A variety of other report example options are outlined in the tables below.

TABLE 2

PICT Reports

| View level | Report type | Implications |
|---|---|---|
| Patient | P1: Includes patient health data from current PICT session. P2: Includes patient health data from one or more previous PICT session(s). | Patient can recall what prior issues were and determine whether they were satisfactorily completed or whether they need to be repeated during current visit. |
| Clinician/Staff | Can view P1, P2 reports. C1: Problem rate index. Look at all issues a patient brings up over time [e.g. (number of issues)/(time between visits)] to get an index of problem rate. May be an indicator for needing augmented care (e.g. case management, complex care | Can serve as "tickler" for busy clinician and staff to ensure that they are providing good "customer service" which is increasingly considered as a quality indicator of practice. Can help staff decide how to streamline clinic procedures to proactively deal with the most common problems/issues. Can help clinic staff to prepare appropriate materials (e.g. written materials, pamphlets) for |

TABLE 2-continued

PICT Reports

| View level | Report type | Implications |
|---|---|---|
| | management) C2: Panel report. Includes issue count across multiple patients (e.g. all of one clinician's patients). | clinic visits (to increase recall) and also to increase training among clinicians/staff to help with recall enhancers. |
| Administrator | A1: See aggregate report for clinicians/clinics or individual patients, by patient issue, service or ways information best received, and/or by total sample or by demographics or clinical characteristics. | Can help administrators determine: What are the top issues? What are the top services domains requested? What are "other" services requested? (by tracking what people put in the "other" free text boxes; this offers an opportunity for a dynamic process to build the repository) What are the top ways people like to receive information? Can help administrators to improve "customer service" which is increasingly considered as a quality indicator of practice. Can help staff decide how to streamline clinic procedures to proactively deal with the most common problems/issues. Can help clinic staff to prepare appropriate materials (e.g. written materials, pamphlets) for clinic visits (to increase recall) and also to increase training among clinicians/staff to help with recall enhancers. Administrator-view of patients, clinicians and clinics. Ensure there are strategies for dealing with top issues - streamline process. |

TABLE 3

IPED Reports

| View level | Report type | Implications |
|---|---|---|
| Patient | P3: Patient "Ask" and "Tell" selections. May include patient's custom, free-form entries. | The patient can use the output to double-check after visit or before next visit whether questions were answered/things told - if not can re-publish for next healthcare contact (or email/call clinic with uncovered issues). By tracking "other" questions/things to tell that patients complete (in "other" free text boxes), an opportunity for a dynamic process exists as a way to build the repository of pre-set questions and answers. |
| Clinician/Staff | C3: Current visit/past visits for a single patient or for overall panel of patients (all of one clinician's patients) | Clinician/staff member can see what questions/issues are most common in their clinic, allowing them to pre-plan with streamlined procedures and materials. This will allow a more streamlined process, which improves efficiency, increases patient (customer) satisfaction and increases quality of care. |
| Administrator | A2: See aggregate report by clinic or by total organization sample, by total sample or by demographics or clinical characteristics. A3. Collection of "other" options from patients at organizational level. | Can determine what the top questions that patients have are - opportunity for quality control and pre-plan organizational approaches with streamlined procedures and materials. This will allow a more streamlined process, which improves efficiency, increases patient (customer) satisfaction and increases quality of care. Can determine what top questions/things to tell by demographics or clinical characteristics. Reports for clinicians and administrators. Helps to predict likely queries for segments of the patient population so that educational materials/pamphlets can be prepared for those segments. Dynamic process for database: collection of "other" questions to update the questions/things to tell or to add new domains. Use of version with check boxes of question items: questions can be selected and may be emailed or texted to patient for their healthcare visit. Or this user interface can exist on a smart phone so that |

TABLE 3-continued

IPED Reports

| View level | Report type | Implications |
|---|---|---|
| | | person can complete and have the delimited set of questions or things to tell on their phone at time of visit. |

TABLE 4

COPICT Reports

| View level | Report type | Implications |
|---|---|---|
| Patient | P4: Includes patient health data from current COPICT session. P5: Includes patient health data from one or more previous COPICT session(s). | Increase awareness among patients and their families of preventative services and guideline-level care. Opportunity for discussion during healthcare visit. Clinician/staff member can correct patient's report once there is resolution: 1) procedure/service actually completed, billed and documented in medical records, but patient not aware. 2) procedure/service not completed - requisition can be given at appointment to increase likelihood that it is actually completed. 3) procedure/service completed but not documented and/or billed. |
| Clinician/Staff | C4: Report pertaining to current visit/past visits for a single patient or for overall panel of patients (all of one clinician's patients) | The patient report sheet can be a "tickler" for busy clinicians and staff to clarify whether procedures/services are completed, recorded and billed and whether patients are appropriately aware of recommended procedures and/or services. Opportunity for education of patients about rationale for procedures/services. Can make changes to way services are administered in clinical panel. Can proactively include questions and education about required services. Clinician/staff member can correct patient's report once there is resolution: 1) procedure/service actually completed, billed and documented in medical records, but patient not aware. 2) procedure/service not completed - requisition can be given at appointment to increase likelihood that it is actually completed. 3) procedure/service completed but not documented and/or billed. Can see overall statistics for panel and/or by demographic or clinical characteristics. Can compare with benchmarks for other clinicians/clinics or overall organization. |
| Administrator | A4: Aggregate report for clinicians/clinics or individual patients. If for individual patients, may be able to identify those patients who have particular difficulty obtaining preventative services. | By resolving discrepancies between automated/billing data and COPICT data, administrators can correct patient-level data so that there is more accurate billing and completion, thus increasing organizational rating and likelihood of receiving incentive payments (e.g. Centers for Medicare and Medicaid Services (CMS) Medicare Advantage Star Rating System). Help in determining who needs care/case management, navigator services or otherwise to ensure that preventive services are offered. Ensures that there is improved quality of care. Helps to prevent "clinical inertia" - failure of providers to begin new medications or increase dosages of existing medications when an abnormal clinical parameter is recorded. Help with clinical or population-based decision-making. |

While various embodiments have been disclosed herein, other aspects and embodiments will be apparent to those skilled in art, with the benefit of this disclosure.

The invention claimed is:

1. A patient information collection method, comprising:
providing, by a computing device, a User Interface (UI) comprising a plurality of fields for identifying patient healthcare issues which a patient desires to address during a visit with the healthcare provider;
receiving, by the computing device, via the fields of the UI, one or more patient identifications of patient healthcare issues, the patient identifications comprising user-entered descriptions of the patient healthcare issues;
for each received patient healthcare issue, providing, by the computing device, a UI comprising a set of patient selectable aspects of care, the set of patient selectable aspects of care including two or more aspects of care from the group comprising:
a diagnosis aspect of care indicating whether the patient desires to address diagnosis of an identified patient healthcare issue during the visit with the healthcare provider;

an information aspect of care indicating whether the patient desires to address information about an identified patient healthcare issue during the visit with the healthcare provider;

a prognosis aspect of care indicating whether a patient desires to address prognosis of an identified patient healthcare issue during the visit with the healthcare provider;

a tests aspect of care indicating whether a patient desires to address tests of an identified patient healthcare issue during the visit with the healthcare provider;

a treatment options aspect of care indicating whether a patient desires to address treatment options of an identified patient healthcare issue during the visit with the healthcare provider;

a medications aspect of care indicating whether a patient desires to address medications for an identified patient healthcare issue during the visit with the healthcare provider;

a refill aspect of care indicating whether a patient desires to address medications refills for an identified patient healthcare issue during the visit with the healthcare provider;

a support aspect of care indicating whether a patient desires to address social support for an identified patient healthcare issue during the visit with the healthcare provider;

a stress aspect of care indicating whether a patient desires to address stress related to an identified patient healthcare issue during the visit with the healthcare provider;

a function aspect of care indicating whether a patient desires to address function related to an identified patient healthcare issue during the visit with the healthcare provider;

a referral aspect of care indicating whether a patient desires to address referral for an identified patient healthcare issue during the visit with the healthcare provider; and a paperwork aspect of care indicating whether a patient desires to address paperwork for an identified patient healthcare issue during the visit with the healthcare provider;

receiving, by the computing device, patient aspect of care selections for each received patient identified patient healthcare issue;

providing, by the computing device, a UI for patient prioritizing of received patient identified patient healthcare issues;

receiving, by the computing device, patient issue prioritizations of the patient identified patient healthcare issues, the patient issue prioritizations comprising a ranking of the patient identified patient healthcare issues;

generating, by the computing device, a report comprising patient prioritized identifications of patient identified patient healthcare issues along with patient selected aspects of care corresponding to each patient identified patient healthcare issue; and storing, by the computing device:
  patient healthcare issues received via the UI comprising the plurality of fields for identifying patient healthcare issues;
  selected aspects of care received via the UI comprising a set of selectable aspects of care;
  data received via a field configured to receive free-form aspect of care descriptions;
  selected information channels received via a UI comprising a set of selectable information channels;
  data received via a field configured to receive free-form information channel descriptions;
  selected questions for a healthcare provider received via a UI comprising a set of selectable questions;
  data received via a field configured to receive free-form healthcare provider questions;
  selected information items for a healthcare provider received via a UI comprising a set of selectable information items; and/or
  data received via a field configured to receive free-form information items for a healthcare provider.

2. The method of claim 1, further comprising providing, by the computing device, an additional UI subsequent to receiving aspect of care selections for each received patient healthcare issue, the additional UI comprising a field for optionally identifying one or more additional patient healthcare issues.

3. The method of claim 1, further comprising providing, by the computing device, a UI comprising a set of selectable information channels, and receiving information channel selections.

4. The method of claim 1, wherein the report is limited to one page.

5. The method of claim 1, wherein generating a report comprises automatically generating two copies of the report for use during the visit with the healthcare provider, including a copy for the patient and a copy for the healthcare provider.

6. The method of claim 1, wherein the report comprises two sections, including a first section and a second section, each section comprising patient identified patient healthcare issues, and wherein the first section comprises patient identified patient healthcare issues of higher patient issue prioritization, and the second section comprises patient identified patient healthcare issues of lower patient issue prioritization, to establish patient and healthcare provider expectations regarding which patient identified patient healthcare issues to address during the healthcare visit.

7. A User Interface (UI) accessible via a display coupled with a computing device, comprising:
  a selectable Patient Information Collection Tool (PICT) control configured to cause the computing device to access and display a PICT, wherein the PICT is configured to receive one or more patient identified patient healthcare issues comprising user-entered descriptions of the patient healthcare issues, and corresponding patient selected aspects of care in preparation for a healthcare visit, and to generate a report comprising prioritized identifications of patient identified patient healthcare issues along with patient selected aspects of care corresponding to each patient healthcare issue; and
  wherein the PICT is configured to display via the UI a set of patient selectable aspects of care for each patient identified patient healthcare issue, and to receive via the UI patient aspect of care selections, the set of patient selectable aspects of care including two or more aspects of care from the group comprising:
    a diagnosis aspect of care indicating whether the patient desires to address diagnosis of an identified patient healthcare issue during the visit with the healthcare provider;
    an information aspect of care indicating whether the patient desires to address information about an identified patient healthcare issue during the visit with the healthcare provider;

a prognosis aspect of care indicating whether a patient desires to address prognosis of an identified patient healthcare issue during the visit with the healthcare provider;

a tests aspect of care indicating whether a patient desires to address tests of an identified patient healthcare issue during the visit with the healthcare provider;

a treatment options aspect of care indicating whether a patient desires to address treatment options of an identified patient healthcare issue during the visit with the healthcare provider;

a medications aspect of care indicating whether a patient desires to address medications for an identified patient healthcare issue during the visit with the healthcare provider;

a refill aspect of care indicating whether a patient desires to address medications refills for an identified patient healthcare issue during the visit with the healthcare provider;

a support aspect of care indicating whether a patient desires to address social support for an identified patient healthcare issue during the visit with the healthcare provider;

a stress aspect of care indicating whether a patient desires to address stress related to an identified patient healthcare issue during the visit with the healthcare provider;

a function aspect of care indicating whether a patient desires to address function related to an identified patient healthcare issue during the visit with the healthcare provider;

a referral aspect of care indicating whether a patient desires to address referral for an identified patient healthcare issue during the visit with the healthcare provider; and a paperwork aspect of care indicating whether a patient desires to address paperwork for an identified patient healthcare issue during the visit with the healthcare provider;

wherein the PICT is configured to store:
  patient identified patient healthcare issues received via a UI comprising a plurality of fields for identifying patient healthcare issues;
  selected aspects of care received via the UI comprising a set of selectable aspects of care;
  data received via a field configured to receive free-form aspect of care descriptions;
  selected information channels received via a UI comprising a set of selectable information channels;
  data received via a field configured to receive free-form information channel descriptions;
  selected questions for a healthcare provider received via a UI comprising a set of selectable questions;
  data received via a field configured to receive free-form healthcare provider questions;
  selected information items for a healthcare provider received via a UI comprising a set of selectable information items; and/or
  data received via a field configured to receive free-form information items for a healthcare provider.

8. A server apparatus configured to provide a Patient Information Collection Tool (PICT), comprising:
  a processor;
  a memory; and
  a PICT stored in the memory and executable by the processor, the PICT comprising:
    a module configured to provide a User Interface (UI) comprising a plurality of fields for identifying patient healthcare issues which a patient desires to address during a visit with the healthcare provider, wherein the fields are configured to receive user-entered descriptions of the patient healthcare issues;
    a module configured to provide a UI comprising a set of selectable aspects of care for each patient healthcare issue identified in the UI for identifying patient issues, the set of patient selectable aspects of care including two or more aspects of care from the group comprising:
      a diagnosis aspect of care indicating whether the patient desires to address diagnosis of an identified patient healthcare issue during the visit with the healthcare provider;
      an information aspect of care indicating whether the patient desires to address information about an identified patient healthcare issue during the visit with the healthcare provider;
      a prognosis aspect of care indicating whether a patient desires to address prognosis of an identified patient healthcare issue during the visit with the healthcare provider;
      a tests aspect of care indicating whether a patient desires to address tests of an identified patient healthcare issue during the visit with the healthcare provider;
      a treatment options aspect of care indicating whether a patient desires to address treatment options of an identified patient healthcare issue during the visit with the healthcare provider;
      a medications aspect of care indicating whether a patient desires to address medications for an identified patient healthcare issue during the visit with the healthcare provider;
      a refill aspect of care indicating whether a patient desires to address medications refills for an identified patient healthcare issue during the visit with the healthcare provider;
      a support aspect of care indicating whether a patient desires to address social support for an identified patient healthcare issue during the visit with the healthcare provider;
      a stress aspect of care indicating whether a patient desires to address stress related to an identified patient healthcare issue during the visit with the healthcare provider;
      a function aspect of care indicating whether a patient desires to address function related to an identified patient healthcare issue during the visit with the healthcare provider;
      a referral aspect of care indicating whether a patient desires to address referral for an identified patient healthcare issue during the visit with the healthcare provider; and
      a paperwork aspect of care indicating whether a patient desires to address paperwork for an identified patient healthcare issue during the visit with the healthcare provider;
    a module configured to provide a UI comprising a set of selectable information channels;
    a module configured to generate a report comprising identifications of patient healthcare issues identified in the UI for identifying patient healthcare issues along with selected aspects of care corresponding to each patient healthcare issue, and further comprising information channel selections identified in the UI for
selecting information channels; and
a backend reporting module configured to generate one
or more reports summarizing patient health data
received via the fields for identifying patient healthcare issues, selectable aspects of care, and selectable information channels;
wherein the server is configured to store:
patient healthcare issues received via the UI comprising a plurality of fields for identifying patient healthcare issues;
selected aspects of care received via the UI comprising a set of selectable aspects of care;
data received via a field configured to receive freeform aspect of care descriptions;
selected information channels received via the UI comprising a set of selectable information channels;
data received via a field configured to receive freeform information channel descriptions;
selected questions for a healthcare provider received via a UI comprising a set of selectable questions;
data received via a field configured to receive freeform healthcare provider questions;
selected information items for a healthcare provider received via a UI comprising a set of selectable information items; and/or
data received via a field configured to receive freeform information items for a healthcare provider.

9. The server apparatus of claim 8, wherein the backend reporting module is configured to generate multi-patient reports summarizing aggregate patient health data corresponding to multiple patients.

10. The server apparatus of claim 9, wherein the backend reporting module is configured to identify the plurality of patients according to a shared patient attribute.

11. The server apparatus of claim 9, wherein the backend reporting module is configured to identify the plurality of patients according to a shared healthcare professional serving the plurality of patients.

12. The server apparatus of claim 9, wherein the backend reporting module is configured to generate a report comprising occurrence rates, among the aggregate patient health data corresponding to multiple patients, of one or more of:
patient issues received via the UI comprising a plurality of fields for identifying patient issues;
selected aspects of care received via the UI comprising a set of selectable aspects of care;
selected information channels received via the UI comprising a set of selectable information channels;
selected questions for a healthcare provider received via a UI comprising a set of selectable questions; and/or
selected information items for a healthcare provider received via a UI comprising a set of selectable information items.

13. The server apparatus of claim 8, wherein the backend reporting module is configured to generate one or more reports comprising a patient problem rate index, the patient problem rate index comprising a number of patient issues associated with a patient or group of patients per unit of time.

14. The server apparatus of claim 8, wherein the backend reporting module is configured to generate a multi-session report comprising patient health data received during a plurality of user sessions, wherein each of the plurality of user sessions comprises a user interaction with one or more of the UI comprising a plurality of fields for identifying patient issues; the UI comprising a set of selectable aspects of care for each identified patient issue; and/or the UI comprising a set of selectable information channels.

* * * * *